United States Patent [19]
Goldfine et al.

[11] Patent Number: 5,968,508
[45] Date of Patent: Oct. 19, 1999

[54] ANTAGONISTS TO INSULIN RECEPTOR TYROSINE KINASE INHIBITOR

[75] Inventors: Ira D. Goldfine, Kentfield; Andrew Grupe, Belmont; Betty A. Maddux, San Francisco; Steven Spencer, San Mateo; Timothy A. Stewart, San Francisco; Denise M. Harrison, Sunnyvale, all of Calif.

[73] Assignee: Regents of the University of California, The, Oakland, Calif.

[21] Appl. No.: 08/504,169

[22] Filed: Jul. 19, 1995

Related U.S. Application Data

[63] Continuation-in-part of application No. PCT/US94/14893, Dec. 28, 1994, which is a continuation-in-part of application No. 08/182,241, Jan. 14, 1994, abandoned.

[51] Int. Cl.⁶ .......................... A61K 39/395; C07K 16/00
[52] U.S. Cl. .................................. 424/130.1; 424/141.1; 530/387.1; 530/388.1
[58] Field of Search .............................. 424/130.1, 141.1; 530/387.1, 388.1

[56] References Cited

U.S. PATENT DOCUMENTS

| | | | |
|---|---|---|---|
| 4,748,018 | 5/1988 | Stolle et al. | 424/157.1 |
| 5,124,147 | 6/1992 | Wissner et al. | 424/145.1 |

OTHER PUBLICATIONS

Stefan, et al. 1996. Diabetes, 45: 980–983.
Borrebaeck, Carl A.K., "Strategy for the production of human monoclonal antibodies using in vitro activated B cells" *J. Immunol. Methods* 123:157–165 (1989).
Buckley et al., "Plasma Cell Membrane Glycoprotein PC–1" *Journal of Biological Chemistry* 265(29):17506–17511 (1990).
Costantino et al., "Insulin–Resistant MDA–MB231 Human Breast Cancer Cells Contain a Tyrosine Kinase Inhibiting Activity" *Molecular Endocrinology* 7(12):1667–1676 (1993).
Elliott et al., "Treatment of Rheumatoid Arthritis With Chimeric Monoclonal Antibodies to Tumor Necrosis Factor α" *Arthritis and Rheumatism* 36(12):1681–1690 (1993).
Funakoshi et al., "Molecular Cloning of cDNAs for Human Fibroblast Nucleotide Pyrophosphatase" *Arch. of Biochem. and Biophys.* 295(1):180–187 (1992).
Goding, "Antibody Production by Hybridomas" *Journal of Immunological Methods* 39:285–308 (1980).
Goldfine, Ira D., "The Insulin Receptor: Molecular Biology and Transmembrane Signaling" *Endocr Rev.* 8(3):235–255 (1987).
Goodman, "Immunogenicity & Antigenic Specificity" *Basic and Clinical Immunology* pp. 32–40 (1976).
Grupe et al., "Inhibition of Insulin Receptor Phosphorylation by PC–1 is Not Mediated by the Hydrolysis of Adenosine Triphosphate or the Generation of Adenosine" *Journal of Biological Chemistry* 270(38):22085–22088 (1995).

Grupe et al., "Transgenic Knockouts Reveal a Critical Requirement for Pancreatic β Cell Glucokinase in Maintaining Glucose Homeostasis" *Cell* 83:69–78 (1995).
Harris et al., "Therapeutic Antibodies—The Coming of Age" *TIBTECH* 11:42–44 (Feb. 1993).
Huang et al., "Expression of the Murine Plasma Cell Nucleotide Pyrophosphohydrolase PC–1 is Shared by Human Liver, Bone, and Cartilage Cells" *J. Clin. Invest.* 94:560–567 (1994).
Itoh et al., "Localization of Prohormone Convertase (PC–1 and PC–2) in the Human and Rat Pancreatic Islets" *Acta Histochem. Cytochem.* (Abstract No. 123) 27(4):406 (1994).
Maddux et al., "Inhibitors of Insulin Receptor Tyrosine Kinase in Fibroblasts from Diverse Patients with Impaired Insulin Action: Evidence for a Novel Mechanism of Postreceptor Insulin Resistance" *J. Clin. Endocrin. Metabol.* 77(1):73–79 (1993).
Maddux et al., "Membrane Glycoprotein PC–1 and Insulin Resistance in Non–Insulin–Dependent Diabetes Mellitus" *Nature* 373:448–451 (1995).
Moller, D.E. & Flier, J.S., "Mechanisms of Disease: Insulin Resistance–Mechanisms, Syndromes and Implications" *New England J. of Medicine* 325(13):938–948 (1991).
Oda et al., "The Plasma Cell Membrane Glycoprotein, PC–1, Is a Threonine–Specific Protein Kinase Stimulated by Acidic Fibroblast Growth Factor" *Journal of Biological Chemistry* 266(25):16791–16795 (1991).
Osband et al., "Problems in the investigational study and clinical use of cancer immunotherapy" *Immunology Today* 11(6):193–195 (1990).
Rebbe et al., "Expression of Nucleotide Pyrophosphatase and Alkaline Phosphodiesterase I Activities of PC–1, the Murine Plasma Cell Antigen" *Molecular Immunology* 30(1):87–93 (1993).
Sbraccia et al., "Production of Inhibitor of Insulin–Receptor Tyrosine Kinase in Fibroblasts from Patient with Insulin Resistance and NIDDM" *Diabetes* 40:295–299 (1991).
Seino S et al., "Perspectives in Diabetes: Human Insulin–Receptor Gene" *Diabetes* 39:129–133 (1990).
Sevier et al., "Monoclonal Antibodies in Clinical Immunology" *Clinical Chemistry* 27(11):1797–1806 (1981).
Stearne et al., "The Murine Plasma Cell Antigen PC–1: Purification and Partial Amino Acid Sequence" *J. Immunol.* 134(1):443–448 (1985).
Waldmann, T., "Monoclonal Antibodies in Diagnosis and Therapy" *Science* 252:1657–1662 (Jun. 1991).

(List continued on next page.)

*Primary Examiner*—Paula K. Hutzell
*Assistant Examiner*—Minh-Tam Davis
*Attorney, Agent, or Firm*—Bozicevic, Field & Francis LLP; Pamela J. Sherwood

[57] ABSTRACT

A method of diagnosing insulin resistance and related disorders is provided. Additionally, methods of treating mammals with insulin resistance and related disorders is provided. The methods employ antagonists to an insulin receptor tyrosine kinase inhibitor protein.

5 Claims, 12 Drawing Sheets

OTHER PUBLICATIONS

Woody et al., "Effective Clinical Therapy of Cardiovascular and Autoimmune Diseases with Chimerized Monoclonal Antibodies" *IBC's Second Annual Int'l Conference on Commercializing Human Monoclonal Antibodies* (abstract only)San Diego, CA:2:35 (1994).

Yano et al., "Immunoaffinity Purification and Characterization of Nucleotide Pyrophosphatase from Human Placenta" *Biochem. and Biophy. Res. Comm.* 147(3):1061–1069 (1987).

Feinstein, R. et al. Dec. 5, 1993. J. Biol. Chem. 268 : 26055–26058.

Osband, M.E. et al. 1990. Immunol. Today 11: 193–195.

Shisheva, A. et al. 1994. Endocrinol. 134: 507–510.

```
Met Glu Arg Asp Gly Cys Ala Gly Gly Ser Arg Gly Gly Glu
 1               5                   10                  15

Gly Gly Arg Ala Pro Arg Glu Gly Pro Ala Gly Asn Gly Arg Asp
               20              25                      30

Arg Gly Arg Ser His Ala Ala Glu Ala Pro Gly Asp Pro Gln Ala
               35              40                      45

Ala Ala Ser Leu Leu Ala Pro Met Asp Val Gly Glu Glu Pro Leu
               50              55                      60

Glu Lys Ala Ala Arg Ala Arg Thr Ala Lys Asp Pro Asn Thr Tyr
               65              70                      75

Lys Val Leu Ser Leu Val Leu Ser Val Cys Val Leu Thr Thr Ile
               80              85                      90

Leu Gly Cys Ile Phe Gly Leu Lys Pro Ser Cys Ala Lys Glu Val
               95              100                     105

Lys Ser Cys Lys Gly Arg Cys Phe Glu Arg Thr Phe Gly Asn Cys
               110             115                     120

Arg Cys Asp Ala Ala Cys Val Glu Leu Gly Asn Cys Cys Leu Asp
               125             130                     135

Tyr Gln Glu Thr Cys Ile Glu Pro Glu His Ile Trp Thr Cys Asn
               140             145                     150

Lys Phe Arg Cys Gly Glu Lys Arg Leu Thr Arg Ser Leu Cys Ala
               155             160                     165

Cys Ser Asp Asp Cys Lys Asp Lys Gly Asp Cys Cys Ile Asn Tyr
               170             175                     180

Ser Ser Val Cys Gln Gly Glu Lys Ser Trp Val Glu Glu Pro Cys
               185             190                     195
```

FIG. IA

```
Glu Ser Ile Asn Glu Pro Gln Cys Pro Ala Gly Phe Glu Thr Pro
                200                 205                 210

Pro Thr Leu Leu Phe Ser Leu Asp Gly Phe Arg Ala Glu Tyr Leu
                215                 220                 225

His Thr Trp Gly Gly Leu Leu Pro Val Ile Ser Lys Leu Lys Lys
                230                 235                 240

Cys Gly Thr Tyr Thr Lys Asn Met Arg Pro Val Tyr Pro Thr Lys
                245                 250                 255

Thr Phe Pro Asn His Tyr Ser Ile Val Thr Gly Leu Tyr Pro Glu
                260                 265                 270

Ser His Gly Ile Ile Asp Asn Lys Met Tyr Asp Pro Lys Met Asn
                275                 280                 285

Ala Ser Phe Ser Leu Lys Ser Lys Glu Lys Phe Asn Pro Glu Trp
                290                 295                 300

Tyr Lys Gly Glu Pro Ile Trp Val Thr Ala Lys Tyr Gln Gly Leu
                305                 310                 315

Lys Ser Gly Thr Phe Phe Trp Pro Gly Ser Asp Val Glu Ile Asn
                320                 325                 330

Gly Ile Phe Pro Asp Ile Tyr Lys Met Tyr Asn Gly Ser Val Pro
                335                 340                 345

Phe Glu Glu Arg Ile Leu Ala Val Leu Gln Trp Leu Gln Leu Pro
                350                 355                 360

Lys Asp Glu Arg Pro His Phe Tyr Thr Leu Tyr Leu Glu Glu Pro
                365                 370                 375
```

FIG. 1B

```
Asp Ser Ser Gly His Ser Tyr Gly Pro Val Ser Ser Glu Val Ile
                380             385                 390

Lys Ala Leu Gln Arg Val Asp Gly Met Val Gly Met Leu Met Asp
                395             400                 405

Gly Leu Lys Glu Leu Asn Leu His Arg Cys Leu Asn Leu Ile Leu
                410             415                 420

Ile Ser Asp His Gly Met Glu Gln Gly Ser Cys Lys Lys Tyr Ile
                425             430                 435

Tyr Leu Asn Lys Tyr Leu Gly Asp Val Lys Asn Ile Lys Val Ile
                440             445                 450

Tyr Gly Pro Ala Ala Arg Leu Arg Pro Ser Asp Val Pro Asp Lys
                455             460                 465

Tyr Tyr Ser Phe Asn Tyr Glu Gly Ile Ala Arg Asn Leu Ser Cys
                470             475                 480

Arg Glu Pro Asn Gln His Phe Lys Pro Tyr Leu Lys His Phe Leu
                485             490                 495

Pro Lys Arg Leu His Phe Ala Lys Ser Asp Arg Ile Glu Pro Leu
                500             505                 510

Thr Phe Tyr Leu Asp Pro Gln Trp Gln Leu Ala Leu Asn Pro Ser
                515             520                 525

Glu Arg Lys Tyr Cys Gly Ser Gly Phe His Gly Ser Asp Asn Val
                530             535                 540

Phe Ser Asn Met Gln Ala Leu Phe Val Gly Tyr Gly Pro Gly Phe
                545             550                 555

Lys His Gly Ile Glu Ala Asp Thr Phe Glu Asn Ile Glu Val Tyr
                560             565                 570
```

FIG. IC

```
Asn Leu Met Cys Asp Leu Leu Asn Leu Thr Pro Ala Pro Asn Asn
                575             580                 585
Gly Thr His Gly Ser Leu Asn His Leu Leu Lys Asn Pro Val Tyr
                590             595                 600
Thr Pro Lys His Pro Lys Glu Val His Pro Leu Val Gln Cys Pro
                605             610                 615
Phe Thr Arg Asn Pro Arg Asp Asn Leu Gly Cys Ser Cys Asn Pro
                620             625                 630
Ser Ile Leu Pro Ile Glu Asp Phe Gln Thr Gln Phe Asn Leu Thr
                635             640                 645
Val Ala Glu Glu Lys Ile Ile Lys His Glu Thr Leu Pro Tyr Gly
                650             655                 660
Arg Pro Arg Val Leu Gln Lys Glu Asn Thr Ile Cys Leu Leu Ser
                665             670                 675
Gln His Gln Phe Met Ser Gly Tyr Ser Gln Asp Ile Leu Met Pro
                680             685                 690
Leu Trp Thr Ser Tyr Thr Val Asp Arg Asn Asp Ser Phe Ser Thr
                695             700                 705
Glu Asp Phe Ser Asn Cys Leu Tyr Gln Asp Phe Arg Ile Pro Leu
                710             715                 720
Ser Pro Val His Lys Cys Ser Phe Tyr Lys Asn Asn Thr Lys Val
                725             730                 735
Ser Tyr Gly Phe Leu Ser Pro Pro Gln Leu Asn Lys Asn Ser Ser
                740             745                 750
```

FIG. ID

Gly Ile Tyr Ser Glu Ala Leu Leu Thr Thr Asn Ile Val Pro Met
            755                 760                 765

Tyr Gln Ser Phe Gln Val Ile Trp Arg Tyr Phe His Asp Thr Leu
            770                 775                 780

Leu Arg Lys Tyr Ala Glu Glu Arg Asn Gly Val Asn Val Val Ser
            785                 790                 795

Gly Pro Val Phe Asp Phe Asp Tyr Asp Gly Arg Cys Asp Ser Leu
            800                 805                 810

Glu Asn Leu Arg Gln Lys Arg Arg Val Ile Arg Asn Gln Glu Ile
            815                 820                 825

Leu Ile Pro Thr His Phe Phe Ile Val Leu Thr Ser Cys Lys Asp
            830                 835                 840

Thr Ser Gln Thr Pro Leu His Cys Glu Asn Leu Asp Thr Leu Ala
            845                 850                 855

Phe Ile Leu Pro His Arg Thr Asp Asn Ser Glu Ser Cys Val His
            860                 865                 870

Gly Lys His Asp Ser Ser Trp Val Glu Leu Leu Met Leu His
            875                 880                 885

Arg Ala Arg Ile Thr Asp Val Glu His Ile Thr Gly Leu Ser Phe
            890                 895                 900

Tyr Gln Gln Arg Lys Glu Pro Val Ser Asp Ile Leu Lys Leu Lys
            905                 910                 915

Thr His Leu Pro Thr Phe Ser Gln Glu Asp
            920                 925

FIG. IE

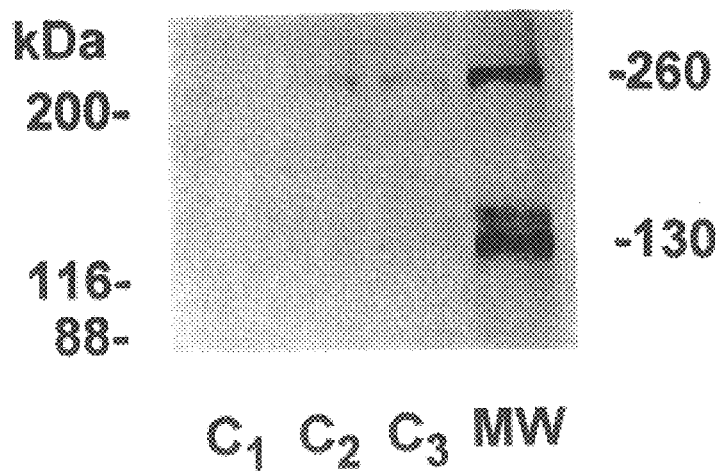
FIG. 4A
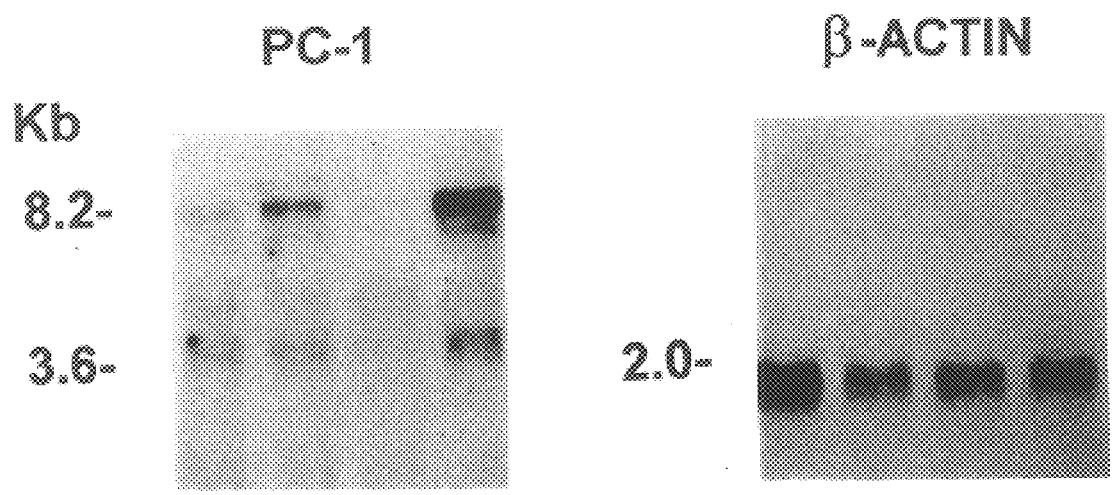
FIG. 4B
FIG. 4C

ANTAGONISTS TO INSULIN RECEPTOR TYROSINE KINASE INHIBITOR

This application is continuation-in-part of International Application No. PCT/US94/14893, filed Dec. 28, 1994, which is a continuation-in-part of U.S. application Ser. No. 08/182,241 filed Jan. 14, 1994.

FIELD OF THE INVENTION

The present invention relates to agents that neutralize the activity of inhibitors of insulin receptor tyrosine kinase activity, especially PC-1, and their uses in the diagnosis and treatment of diseases and disorders involving inappropriate insulin receptor tyrosine kinase inhibitor expression. In particular the invention relates to agents useful in detecting or treating diseases or disorders associated with an inappropriate expression of PC-1. In a preferred aspect, the invention relates to agents and methods useful in diagnosing the presence of insulin resistance in an individual suspected of having insulin resistance or related disorders, in particular, noninsulin dependent diabetes mellitus. The invention also provides for methods of treating mammals, preferably humans, who suffer from diseases associated with inappropriate expression of PC-1. In a particular embodiment, the invention provides for methods of preventing, treating, or suppressing the effects of inappropriate expression of PC-1, such as insulin resistance and non-insulin dependent diabetes mellitus.

DESCRIPTION OF RELATED ART

Diabetes mellitus in humans is a complex disorder which can be subdivided into two major clinical syndromes. Each category, in turn, subsumes a number of differing etiologies. About 10% of persons with diabetes have insulin-dependent diabetes mellitus (IDDM). IDDM is characterized by selective destruction of insulin-producing β cells, absolute insulin deficiency, youthful onset, and evidence of autoimmune pathogenesis. Noninsulin-dependent diabetes mellitus (NIDDM) is more common and often seen in the context of obesity. NIDDM is characterized by onset in middle age, resistance to the effects of insulin, and relative insulin deficiency without β cell destruction. The terms Type 1 and Type 2 diabetes have been used to refer to IDDM and NIDDM respectively. It has been suggested, however, that the terms be used as modifiers of the physiological states, i.e., Type 1 is sometimes used to describe an immune mediated pathogenic mechanism and Type 2 used to describe a non-immune mediated pathogenesis. In Type 1 diabetes, for example, the immune system mediates destruction of beta cells. Using this classification there are three major clinal syndromes: Type 1 insulin dependent diabetes, 2) Type 1 noninsulin dependent diabetes, and 3) Type 2 noninsulin dependent diabetes. The NIDDM stage of Type 1 then would describe the late, slower progressing autoimmune onset.

The pathogenesis of Type 2 NIDDM has not previously been clearly understood. Descriptively, three phases can be recognized in individuals. The first phase is characterized by demonstrable insulin resistance with normal plasma glucose levels and elevated plasma insulin levels. In the second stage, postprandial hyperglycemia and increased insulin resistance characterize the disease. In the third phase, insulin resistance continues and secreted insulin levels decline resulting in fasting hyperglycemia. In all stages the plasma levels of insulin do not correspond to plasma glucose levels, i.e. relative insulin deficiency is perceived. Type 2 NIDDM is typified, therefore, by insulin resistance, as well as, insulin secretory defects. (*Harrison's. Prncpls. of Int. Med.,* 11th Ed., McGraw-Hill, publisher, New York, N.Y.)

Several recent studies suggest that the presence of insulin resistance precedes the onset of NIDDM. Patients with NIDDM secrete insulin, but not in a normal fashion, and have resistance to both endogenous and exogenous insulin in muscle and other insulin sensitive tissues. Moller et al., *N. Eng. J. Med,* 325:938 (1991). The presence of insulin resistance suggests that it may be an initial abnormality in the disease. In the majority of patients with NIDDM, however, the molecular basis of the insulin resistance is unknown.

Dermal fibroblasts, derived from a patient exhibiting insulin resistance and NIDDM, produced an inhibitor of insulin receptor tyrosine kinase activation. Insulin receptor content was normal in the patient and purified insulin receptors had normal tyrosine kinase activity. The inhibitor was shown to be a glycoprotein exhibiting relative specificity toward insulin receptor tyrosine kinase. Sbraccia et al., *Diabetes,* 40:295 (1991) and Maddux et al., *J. Clin. End. Metab.,* 77:73 (1993).

Insulin Receptor

The cellular response to insulin is mediated through the insulin receptor, which is a tetrameric protein consisting of two identical extracellular alpha-subunits which bind insulin and two identical transmembrane beta-subunits which have intracellular tyrosine kinase activity. Goldfine, *Endocr. Rev.,* 8:235 (1987). When insulin binds to the alpha-subunit, the beta-subunit tyrosine kinase is activated and insulin action ensues. Patients with NIDDM have impaired insulin receptor tyrosine kinase activity in muscle, fibroblast and other tissues. Abnormalities in the sequence of the insulin receptor gene do not appear to be the cause of the decreased kinase activity in the vast majority of patients examined. Seino et al., *Diabetes* 39:129 (1990).

Plasma Cell Membrane Glycoprotein PC-1

PC-1 is a class II (cytoplasmic N terminus) membrane glycoprotein; it is the same protein as liver nucleoside pyrophosphatase/alkaline phosphodiesterase I (NPPase). Rebbe et al., *Mol. Immuno.,* 30:87–93 (1993). Monoclonal antibodies recognizing human placental NPPase have been prepared (Yano et al., (1987) Biochem. Biophys. Res. Commun. 147:1061–1067) and used to purifiy NPPase from human placenta (Funakoshi, I., et al., (1992) 295:180–187). PC-1 has been detected in other cells including: placenta; chondrocytes; epididymis; kidney tubules; salivary ducts; brain capillaries; skin fibroblasts; myeloma cells; skeletal muscle; and fat Rebbe et al., *Mol. Immuno.,* 30:87–93 )1993). The size of PC-1 is 115–135 kDa, depending on the tissue studied; PC-1 also exists as a 230–260 kDa dimer. Human PC-1 has been deduced to have 873 amino acids, and is mapped to the chromosome location, 6q22–6q23, Funakoshi et al., *Arch. Biochem. Biophys.,* 295:180–187 (1992). The extracellular domain of PC-1 cleaves phosphosulfate, pyrophosphate, and phosphodiester linkages. PC-1 may have threonine-specific protein kinase activity Oda et al., *J. Biol. Chem.,* 266:16791–16795 (1991). PC-1 has been reported to be closely associated with the acid fibroblast growth factor receptor Oda et al., *J. Biol. Chem.,* 266:16791–16795 (1991), and regulated by TGF-β Huang et al., *J. Clin. Invest.,* 94:560–567 (1994).

Current Treatment of Insulin Resistance and Related Disorders

Current treatment regimes for insulin resistance and diabetes include dietary regimes as well as insulin therapy for patients with IDDM and NIDDM patients who do not respond to dietary changes. Dietary regimes are based on calculations of total caloric intake required for ideal body weight as well as decisions based on fractional distribution of the diet between fat, carbohydrate and protein. However, foods of similar weight and protein, carbohydrate, and fat content do not give rise to similar postprandial blood glucose levels. Therefore, substitution charts often relied on in diet protocols are increasingly questionable. Moreover these dietary charts do not take into account changes in postprandial blood glucose levels that may result from particular combinations of ingested foods.

Insulin therapy is required for all patients with IDDM and for patients with NIDDM that do not respond to dietary changes. There are no standard treatment protocols for patients with insulin therapy although one of several typical regimes is usually indicated. Conventional insulin therapy involves one or two injections of insulin per day. Therapy is usually conducted on an out patient basis with moderate problems in patient compliance.

Nontypical treatments exist for diabetes which include pancreatic transplant. In addition, autoimmune regulation of diabetes is being extensively studied. However the currently available immunosupressives such as cyclosporine and FK506 are usually not warranted.

There is a need therefore, for effective agents that can be used in the diagnosis and therapy of individuals with insulin resistance or NIDDM that offer both ease of use, as well as effective course of therapy.

It is an object of this invention to provide agents useful in various diagnostic and therapeutic methods for the detection and treatment of insulin resistance and related disorders.

SUMMARY OF THE INVENTION

The present invention relates to the diagnosis and treatment of diseases and disorders resulting from an inhibition of insulin receptor tyrosine kinase activity. The invention provides for agents useful in detecting or treating diseases or disorders involving inappropriate inhibition of insulin receptor tyrosine kinase activity.

The present inventors have discovered that certain individuals with insulin resistance overexpress an endogenous inhibitor of insulin receptor tyrosine kinase activity which they have identified as the membrane glycoprotein PC-1. The identification of the inhibitor of insulin receptor tyrosine kinase activity has allowed the present inventors to discover agents and methods useful in detecting and treating diseases and disorders associated with inhibitors of insulin receptor tyrosine kinase activity.

Therefore, in one embodiment the present invention provides a method for detecting or measuring the amount of an insulin receptor tyrosine kinase inhibitor in a sample comprising the steps of; contacting the sample with a first anti-inhibitor antibody under conditions which allow immunospecific binding to occur; (b) contacting the sample with a second anti-inhibitor antibody under conditions which allow immunospecific binding to occur; and (c) detecting or measuring any immunospecific binding that occurs between a component of the sample and both the first and the second anti-inhibitor antibodies, in which immunospecific binding of a component of the sample with said first and second antibodies indicates the presence or amount of the inhibitor in the sample. In a preferred embodiment the insulin receptor tyrosine kinase inhibitor is PC-1.

In another embodiment, the invention provides for a method for detecting the overexpression of an insulin receptor tyrosine kinase inhibitor in a sample comprising the steps of (a) measuring the total amount of an insulin receptor tyrosine kinase inhibitor in the sample according to the methods presented herein and; (b) comparing the amount determined in step (a) to an amount of insulin receptor tyrosine kinase inhibitor present in a standard sample, an increased level in the amount of step (a) being indicative of an overexpression of the insulin receptor tyrosine kinase inhibitor. In a preferred embodiment the insulin receptor tyrosine kinase inhibitor is PC-1.

In another preferred embodiment the invention provides for a method for detecting the presence or the onset of a disease or disorder associated with an overexpression of a PC-1 molecule comprising the steps of (a) measuring the amount of PC-1 in a sample according to the methods presented herein, and (b) comparing the amount of PC-1 in the sample to the amount of PC-1 in a standard sample, an increase in the amount of PC-1 in the sample being indicative of a disease or disorder. The invention thus provides for a method of diagnosing a disease or disorder associated with increased levels of an insulin receptor tyrosine kinase inhibitor, especially PC-1. In preferred aspects, the invention provides for diagnosing a disease associated with an overexpression of PC-1 such as insulin resistance, including non-insulin dependent diabetes mellitus.

In further embodiments, the invention provides for kits for assaying for the detection of increased amounts of an insulin receptor tyrosine kinase inhibitor such as PC-1. The kits of the instant invention are useful in diagnosing a disease or disorder associated with PC-1 expression, such as insulin resistance and non-insulin dependent diabetes mellitus.

In a further embodiment the invention provides for a method of neutralizing the effect of an insulin receptor tyrosine kinase inhibitor which comprises providing an agent capable of neutralizing the effect of an inhibitor on insulin receptor tyrosine kinase activity. In one embodiment the agent is an antibody and the method is performed in vitro. In a preferred embodiment the agent is an antibody, preferably a monoclonal antibody, and the method is performed in vivo. Preferably, according to this aspect of the invention, the antibody is compatible with the host immune system. In this aspect of the invention, when the subject is a human the antibody is preferably a human or humanized antibody.

In another embodiment, the invention provides a method of treating a mammal with a disease or disorder associated with PC-1 expression which comprises providing for an agent effective in neutralizing the effect of PC-1 on the insulin receptor tyrosine kinase activity. The agent is, in a preferred embodiment an antibody capable of binding to and preventing the effect of the PC-1 on insulin receptor tyrosine kinase activity.

In yet another embodiment the invention provides for a pharmaceutical composition comprising an agent capable of neutralizing the effect of an inhibitor of insulin receptor tyrosine kinase activity such as PC-1 along with a suitable pharmaceutical excipient.

DESCRIPTION OF THE DRAWINGS

FIG. 1 (SEQ ID NO: 1) shows the amino acid sequence of the insulin receptor tyrosine kinase inhibitor PC-1.

FIG. 2 is a comparison of insulin receptor autophosphorylation in fibroblasts from a patient with insulin resistance and NIDDM and an age and sex matched control. The fibroblasts from the patient with insulin resistance and NIDDM (MW) required significantly more insulin to stimulate autophosphorylation.

FIG. 3 is polyacrylamide gel showing the inhibitor PC-1 purified from the fibroblasts of a patient with insulin resistance and NIDDM. The lane marked WGA is a sample of material purified over a wheat germ agglutinin agarose column. The lane marked 1M NaCl elution shows the same material eluted from an ATP agarose column. The PC-1 elutes as two bands with relative molecular weights of 130 and 260 kDa.

FIGS. 4A–4C:

FIG. 4A is a Western blot analysis of PC-1 content in fibroblasts of a patient with NIDDM and insulin resistance (lane MW), compared with equivalent controls (lanes C1, C2, and C3). The Western blot reveals a 5–10 fold increase in the levels of PC-1 in the fibroblasts of the patient with insulin resistance and NIDDM.

FIG. 4B: FIG. 4B is a Northern blot analysis of PC-1 message in fibroblast cells of the patient sample MW and the three control samples (C1, C2, and C3).

FIG. 4C: FIG. 4C is a Northern blot analysis of the same samples as 4B probed with cDNA to β-actin showing no change in the level of message. The 8.2 and 3.6 Kb species of the insulin receptor mRNA, and the 2.0 Kb species of the actin mRNA are shown.

FIG. 5A: PC-1 activity in dermal fibroblasts from NIDDM patients and controls as determined by hydrolysis of the synthetic substrate 3'-phosphoadenosine, 5'-phosphosulfate (PAPS).

FIG. 5B: PC-1 content in dermal fibroblasts from NIDDM patients (D1–D4) and controls (C1–C3) as demonstrated by Western blot analysis. The 130 and 260 forms of PC-1 are indicated.

FIG. 5C: Insulin receptor β-subunit autophosphorylation in fibroblasts from 2 NIDDM patients (NIDDM 2 and NIDDM 4) and matched controls (control). The results are presented as a bar graph representing the results obtained from an autoradiograph.

FIG. 6A: A competition-inhibition plot is shown demonstrating the lack of an effect of PC-1 overexpression in MCF-7 cells on insulin binding.

FIG. 6B: Inhibitory effect of PC-1 overexpression in MCF-7 cells on insulin stimulated tyrosine kinase activity as demonstrated by Western blot analysis. MCF-7 cells transfected with PC-1 (MCF-7 PC-1) and MCF-7 cells transfected with pRKneo (MCF-7 NEO). The locations of the insulin receptor β subunit and IRS-1(pp 185) are shown.

FIG. 6C: Effect of PC-1 overexpression in MCF-7 cells on insulin stimulated [$^3$H]thymidine incorporation. In MCF-7 NEO cells, basal incorporation was 19.9±1.8 (mean±SEM, n=4), and in the presence of 1 mM insulin was 36.6±4.7. In MCF-7 PC-1 cells basal incorporation was 15.0±1.9, and in the presence of 1 mM insulin was 34.2±4.2. Results are mean±SEM of 4 separate experiments.

Definitions

Figure 2:
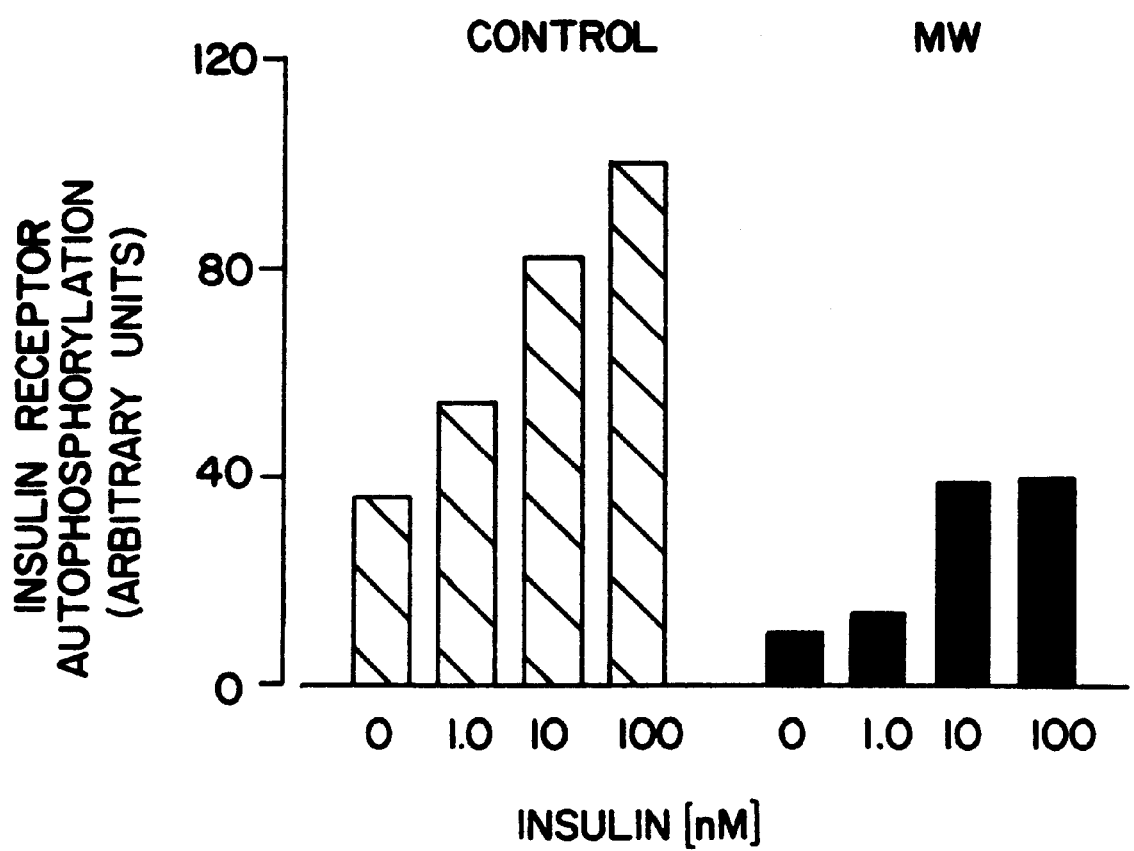
FIG. 2.

The term "treatment" in the instant invention is meant to include therapeutic treatment, as well as prophylactic, or suppressive measures for the disease or disorder. Thus, for example, in the case of NIDDM, successful administration of the agent prior to onset of the disease results in "treatment" of the disease. As another example, successful administration of the agent after clinical manifestation of the disease to combat the symptoms of the disease comprises "treatment" of the disease. "Treatment" also encompasses administration of the agent after the appearance of the disease in order to eradicate the disease. Successful administration of the agent after onset and after clinical symptoms have developed, with possible abatement of clinical symptoms and perhaps amelioration of the disease, comprises "treatment" of the disease.

Those "in need of treatment" include mammals already having the disease or disorder, as well as those prone to having the disease or disorder, including those in which the disease or disorder is to be prevented.

A "disease involving inappropriate expression of PC-1" within the scope of the present invention is meant to include diseases or disorders characterized by an overabundance of the membrane glycoprotein PC-1. This overabundance may be due to any cause including, but not limited to, overexpression at the molecular level, prolonged or accumulated appearance at the site of action, or increased activity of the glycoprotein relative to normal. Such an overabundance can be measured relative to normal expression, appearance, or activity of the PC-1 according to, but not limited to, the assays demonstrated herein. Such disorders may include insulin resistance, and abnormal glucose tolerance, as well as the many disorders in which insulin resistance plays a key role such as obesity, diabetes mellitus, ovarian hyperandrogenism, and hypertension. The disease or disorder for treatment according to the methods presented herein are preferably those diseases where insulin resistance is present due to an overexpression of PC-1. Therefore, in a preferred embodiment, the disease or disorder is insulin resistance, preferably NIDDM, and more preferably Type 2 NIDDM.

The expressions, "agent", "agent that neutralizes the activity of an insulin receptor tyrosine inhibitor", and "an agent specific for an inhibitor of insulin receptor tyrosine kinase activity" within the scope of the present invention are meant to include any molecule which blocks or prevents the interaction between PC-1 and the membrane associated insulin receptor tyrosine kinase. Such agents accomplish this effect in various ways. For instance, one class of agents will bind to PC-1 with sufficient affinity and specificity to neutralize PC-1 such that it has no effect on the insulin receptor tyrosine kinase. Included within this group of agents are antibodies. Another class of agents are molecules based on a protein-protein interaction between the inhibitor, such as PC-1, and the insulin receptor. Such molecules include fragments of the insulin receptor or small bioorganic molecules, e.g. peptidomimetics, that will prevent the interaction between the membrane associated insulin receptor and the inhibitor. Non-limiting examples of selected agents include antibodies, proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like. Another class of agents blocks or prevents intracellular or membrane associated events occurring between the insulin receptor and the insulin receptor tyrosine kinase inhibitor. In a preferred embodiment the agent is an antibody, which antibody has the desirable properties of binding to an inhibitor such as PC-1 and preventing its interaction with the membrane associated insulin receptor. In another preferred aspect the agent is a soluble receptor based on the primary structure of the insulin receptor which has the desirable qualities of preventing the interaction of the membrane associated insulin receptor with the inhibitor of tyrosine kinase activity while being unable to bind free insulin in vivo. In another preferred embodiment the agent is a bioorganic molecule capable of preventing the interaction between the PC-1 and the insulin receptor. In another aspect of the invention the "agent" is a transcriptional regulator of PC-1 expression.

The term "inhibitor" as used herein is meant to include any molecule which, by virtue of its association with the insulin receptor or insulin receptor signalling pathway brings about an insulin insensitivity. In a preferred aspect of the present invention, the inhibitor is the membrane glycoprotein PC-1 described in Buckley et al., *J. Biol. Chem.*, 265(29): 17506–17511 (1990). The corresponding protein has been described in other species, for instance, murine, Van Driel et al., *PNAS*, 82:8619–8623 (1985). The present invention is meant to include the human molecules as well as those of other species.

The terms "neutralize", and "neutralize the activity of" are used herein to mean, for example, block, prevent, reduce, counteract the activity of, or make the inhibitor ineffective by any mechanism. Therefore, the agent may prevent a binding event necessary for inhibition of insulin receptor tyrosine kinase activity. By "neutralizing antibody" is meant an antibody molecule as herein defined which is able to block or significantly reduce an effector function of the inhibitor. For example, a neutralizing antibody may inhibit or reduce the ability of PC-1 to interact with the insulin receptor to decrease tyrosine kinase activity. Alternatively, the neutralizing antibody may inhibit or reduce the ability of PC-1 to block the insulin receptor signalling pathway. The neutralizing antibody may also immunospecifically bind to the inhibitor such as PC-1 in an immunoassay for inhibitor activity such as the ones described herein. It is a characteristic of the "neutralizing antibody" of the invention that it retain its functional activity in both in vitro and in vivo situations. The term "antibody" is used in the broadest sense and specifically covers single anti-inhibitor monoclonal antibodies and anti-inhibitor antibody compositions with polyepitopic specificity (including neutralizing and non-neutralizing antibodies). The term "antibody" is also meant to include both intact molecules as well as fragments thereof which bind the inhibitor, such as, for example, F(ab')$_2$, Fab', Fab and Fv. These fragments lack the Fc fragment of an intact antibody molecule, clear more rapidly from the circulation, and may have less non-specific tissue binding than an intact antibody, Wahl et al., *J. Nucl. Med.*, 24:316–325 (1983), properties which may be desirable for particular therapeutic or diagnostic utilities. It will be appreciated that these antigen-binding fragments of the antibodies useful in the present invention may be used for the detection and quantitation of inhibitor proteins or peptides as disclosed herein for intact antibody molecules. Such fragments are typically produced by proteolytic cleavage, using enzymes such as papain (to produce Fab fragments) or pepsin (to produce F(ab')$_2$ fragments) or by reducing the disulfide bridges.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies herein include hybrid and recombinant antibodies produced by splicing a variable (including hypervariable) domain of an anti-inhibitor antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments [e.g., Fab, F(ab)$_2$, and Fv], so long as they exhibit the desired biological activity. See, e.g. U.S. Pat. No. 4,816,567 and Mage & Lamoyi, in *Monoclonal Antibody Prod. Techniques and Applns*, pp.79–97 (Marcel Dekker, Inc.), N.Y. (1987).

For example, the monoclonal antibodies to be used in accordance with the present invention may be made by the hybridoma method first described by Kohler & Milstein, *Nature*, 256:495 (1975), or may be made by recombinant DNA methods (U.S. Pat. No. 4,816,567). The "monoclonal antibodies" may also be isolated from phage libraries generated using the techniques described in McCafferty et al., *Nature*, 348:552–554 (1990), for example.

"Humanized" forms of non-human (e.g. murine) antibodies are specific chimeric immunoglobulins, immunoglobulin chains or fragments thereof (such as Fv, Fab, Fab', F(ab)$_2$ or other antigen-binding subsequences of antibodies) which contain minimal sequence derived from non-human immunoglobulin. For the most part, humanized antibodies are human immunoglobulins (recipient antibody) in which residues from the complementary determining regions (CDRs) of the recipient antibody are replaced by residues from the CDRs of a non-human species (donor antibody) such as mouse, rat or rabbit having the desired specificity, affinity and capacity. In some instances, Fv framework region (FR) residues of the human immunoglobulin are replaced by corresponding non-human FR residues. Furthermore, the humanized antibody may comprise residues which are found neither in the recipient antibody nor in the imported CDR or FR sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR residues are those of a human immunoglobulin consensus sequence. The humanized antibody optimally also will comprise at least a portion of an immunoglobulin constant region (Fc), typically that of a human immunoglobulin.

The term "sample" as used herein, refers to a biological sample containing or suspected of containing an insulin receptor tyrosine kinase inhibitor. This sample may come from any source, preferably a mammal and more preferably a human. Such samples include aqueous fluids such as serum, plasma, lymph fluid, synovial fluid, follicular fluid, seminal fluid, milk, whole blood, urine, cerebrospinal fluid, saliva, sputum, tears, perspiration, mucous, tissue culture medium, tissue extracts, and cellular extracts.

The term "mammal" for the purposes of treatment refers to any animal classified as a mammal, including but not limited to, humans, sport, zoo, pet and domestic or farm animals such as dogs, cats, cattle, sheep, pigs, horses, and primates, such as monkeys. Preferably the mammal is a human.

DETAILED DESCRIPTION OF THE INVENTION

The present inventors have identified an inhibitor of insulin receptor tyrosine kinase, present in fibroblasts of certain insulin resistant individuals, as the class II membrane glycoprotein PC-1. The present inventors have also discovered that PC-1 activity is increased in fibroblasts of patients with NIDDM. Based on this discovery, the present inventors have designed novel methods of diagnosing and treating diseases and disorders involving inappropriate expression of membrane glycoprotein PC-1 based on agents which neutralize the activity of PC-1 as it effects the insulin receptor. Therefore, the present invention provides for agents useful in a number of in vitro and in vivo diagnostic and therapeutic situations. The present invention also provides for methods of using the agents in the diagnosis and treatment of diseases and disorders associated with inappropriate PC-1 expression. The invention will now be described with respect to these agents. The invention will also be illustrated by the methods of using the agents in in vitro and in vivo applications.

1. Agents

In the broadest aspect, the agents of the present invention, by virtue of their interaction with inhibitors of insulin receptor tyrosine kinase activity, prevent or block the inhibition of tyrosine kinase activity. The agents of the invention are based on the discovery that PC-1 inhibits tyrosine kinase activity in patients with insulin resistance. Therefore, the agents of the invention neutralize the ability of PC-1 to inhibit insulin receptor tyrosine kinase activity. Although the present inventors do not wish to be bound by scientific theory the agents of the invention may block or prevent the interaction of the inhibitor with the insulin receptor tyrosine kinase activity. On the other hand, the agent may block or prevent the interaction of an inhibitor with the insulin receptor signalling pathway. Additionally, there are at least two mechanisms by which PC-1 may inhibit insulin action, i.e., dependent on insulin receptor phosphorylation, or not dependent on insulin receptor phosphorylation. Agents which effect either of these two mechanisms are meant to be included within the scope of the present invention.

2. Antibody Agents

In a preferred aspect "agent" within the scope of the present invention is meant to include antibodies. In a preferred embodiment the antibody of the invention is directed against the inhibitor and, by virtue of immunospecific binding prevents the interaction between the inhibitor and the insulin receptor.

3. Preparation of Anti-Inhibitor Antibodies

According to this aspect of the invention antibodies are isolated that are reactive with PC-1 and additionally block or prevent PC-1 interaction with the insulin receptor.

4. Polyclonal antibodies

Polyclonal antibodies to PC-1 molecules or fragments thereof are generally raised in animals by multiple subcutaneous (sc) or intraperitoneal (ip) injections of PC-1 or PC-1 fragments and an adjuvant. The full length amino acid sequence of PC-1 is provided in FIG. 1, SEQ ID NO 1. The full length protein or any immuno-dominant fragment can be used as an immunogen. It may be useful to conjugate PC-1 or a fragment containing the target amino acid sequence to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the PC-1 polypeptides or fragments, immunogenic conjugates, or derivatives by combining 1 mg or 1 μg of the peptide or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for PC-1 or PC-1 fragment antibody titer. Animals are boosted until the titer plateaus. Preferably, the animal is boosted with the conjugate of the same PC-1 or PC-1 fragment, but conjugated to a different protein and/or through a different cross-linking reagent. Conjugates also can be made in recombinant cell culture as protein fusions. Also, aggregating agents such as alum are suitably used to enhance the immune response.

5. Monoclonal antibodies

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the anti-PC-1 monoclonal antibodies of the invention may be made using the hybridoma method first described by Kohler and Milstein, *Nature*, 256:495 (1975), or may be made by recombinant DNA methods (U.S. Pat. No. 4,816,567).

In the hybridoma method, a mouse or other appropriate host animal, such as a hamster, is immunized as herein described to elicit lymphocytes that produce or are capable of producing antibodies that will specifically bind to the PC-1 or PC-1 fragment used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Prncpls. and Practice*, pp.59–103, Academic Press, (1986).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Maryland USA.

Culture medium in which hybridoma cells are growing is assayed for production of monoclonal antibodies directed against PC-1.

6. Screening for Antibody Agents

Screening for antibody agents useful in the context of the present invention will usually be a multistep process. In one embodiment, the antibodies of the present invention have the desirable characteristics of binding the PC-1 molecule with reasonably high affinity and specificity. Additionally, the antibodies of the invention will, preferably, prevent or block the interaction between PC-1 and the membrane associated insulin receptor such that tyrosine kinase activity of that receptor is not affected. Preferably, screening for useful antibodies is performed with the goal of isolating antibodies with one or both the desirable qualities of an antibody agent.

Specific in vitro binding assays, such as the ones described below, can be used to isolate antibodies reactive with PC-1.

A preferred way of measuring the reactivity of a PC-1 epitope with a specific antibody of the present invention is by enzyme immunoassay (EIA) such as an enzyme-linked immunosorbent assay (ELISA), Voller, A. et al., *J. Clin. Pathol.*, 31:507–520 (1978); Butler, J. E., *Meth. Enzymol.* 73:482–523 (1981); Maggio, E. (ed.), *Enzyme Immunoassay,* CRC Press, Boca Raton, Fla., (1980). The enzyme, when exposed to an appropriate substrate, will react with the substrate in such a manner as to produce a chemical moiety which can be detected, for example, by spectrophotometric, fluorimetric or by visual means.

Detection of PC-1 may be accomplished using any of a variety of other immunoassays. For example, it is possible to detect antibody binding to PC-1 through the use of a radioimmunoassay (RIA). See, for example, Weintraub, B., *Prncpls. of Radioimmunoassay,* 7th Training Course on Radioli-gand Assay Techniques, The Endocrine Society, (March, 1986) pp. 1–5, 46–49 and 68–78; Work, T. S. et al., *Laboratory Techniques and Biochemistry in Molecular Biology,* North Holland Publishing Company, (New York, 1978).

Additional types of immunoassays include precipitation reactions, gel diffusion precipitation reactions, immunodiffusion assays, agglutination assays, complement fixation assays, immunoradiometric assays, protein A immunoassays, and immunoelectrophoresis assays.

In a typical screening procedure wells of flat bottomed 96 well plates are coated overnight at 4° C. with 100 μl of goat anti-mouse IgG Fc-specific antibodies (Cappel, Westchester, Pa.) at 2 μg/ml in PBS. After blocking plates for 1 hr with a solution of 1% BSA in PBS, plates are washed with wash buffer (0.05w Tween-20 in PBS). Hybridoma culture supernatants (100 μl) are added and incubated for 1–2 hrs at room temperature. The wells are then washed with wash buffer, and 100 μl of a solution containing approximately 1 μg/ml soluble PC-1, horseradish peroxidase-conjugated anti-PC-1 Fc fragment, 2% normal mouse serum, 0.256 NP-40, and 25% FCS in wash buffer are added and incubated for 2 hr. After washing, the reactions are developed. Wells positive for PC-1 antibodies are selected for further characterization.

Alternatively, wells of flat bottomed 96 well plates are coated overnight at 4° C. with 100 μl of a solution containing purified PC-1 or a fragment thereof at 2 gμg/ml in PBS. After blocking plates for 1 hr with a solution of 1% BSA in PBS, plates are washed with wash buffer (0.05% Tween-20 in PBS). Hybridoma culture supernatant (100 μl) are added and incubated for 1–2 hrs at room temperature. The wells are then washed with wash buffer, and 100 Al of a solution containing approximately 1 μg/ml horseradish peroxidase-conjugated goat anti-mouse specific antibodies (Cappel, Westchester, Pa.) 26 normal mouse serum, 0.25% NP-40, and 25% FCS in wash buffer are added and incubated for 2 hr. After washing, the reactions are developed. Wells positive for PC-1 antibodies are selected for further characterization.

Once an antibody is isolated that reacts with the PC-1 molecule, it is desirable to screen the hybridomas for their effectiveness in neutralizing the inhibitor activity of PC-1 for insulin receptor tyrosine kinase.

To isolate a neutralizing antibody, antibodies are made using the techniques for generating these molecules elaborated above. The preferred neutralizing antibody is non-immunogenic in a human and directed against a single determinant. Following production of a panel of antibodies, the molecules are subjected to a screening process in order to identify those molecules which meet the desired criteria (i.e. which are able to neutralize a biological activity of PC-1 either in vitro or in vivo). Normally, samples of PC-1 will be exposed to the panel of anti-PC-1 antibodies and will then be subjected to the assays described herein. Those antibodies which block the ability of PC-1 to inhibit insulin receptor tyrosine kinase activity can be selected as neutralizing antibodies.

Assaying for potential neutralizing antibodies can be accomplished in a number of ways. In particular, the neutralizing activity of the antibody agent of the invention against the inhibitor can be assessed by measuring whether the antibody agent can block the PC-1 induced decrease in insulin receptor tyrosine kinase activity as measured by insulin receptor autophosphorylation as well as phosphorylation of the exogenous substrate poly(Glu-Tyr) (Example 1). Standard methods for carrying out the assay are reported in Sbraccia et al., *J. Biol. Chem.* 265:4902–4907, (1990). According to this procedure, hybridoma supernatants are screened for their ability to effect insulin receptor autophosphorylation. In one such assay, the human breast carcinoma cell line MCF-7, Milazzo et al., *Cancer Rsch.,* 52:3924–3930 (1992), is transfected with an expression plasmid containing PC-1 cDNA. MCF-7 cells which express PC-1 have a decreased insulin receptor tyrosine kinase activity as measured by insulin receptor autophosphorylation. Hybridoma supernatants can be incubated with MCF-7 cells transfected to express PC-1 and assayed according to known methods for measuring autophosphorylation of the insulin receptor. In a preferred method, transfected MCF-7 cells are coated onto 10 cm. plates in 100 μl of media and cultured overnight at 37° C. in a humidified atmosphere. The wells are lightly tapped to remove the culture media and 100 μl of hybridoma supernatant is added to the wells. The wells are incubated for an additional 30 minutes in the presence of insulin and the excess hybridoma media is decanted. Next, the MCF-7 cells are lysed to solubilize the insulin receptors. Lysis is conducted in the presence of phosphatase inhibitors in a buffer consisting of 150 mM NaCl containing 50 mM HEPES, 0.5% TRITON® X-100, 0.01% thimerosal, 30 KIU/ml aprotinin, 1 mM 4-(2-aminoethyl)-benzenesulfonyl fluoride hydrochloride, 50CM leupeptin, and 2 mM sodium orthovanadate, pH 7.5. The lysates are then screened for the presence of phosphotyrosine using a standard ELISA procedure.

In the subsequent ELISA, insulin receptors are captured on a 96 well plate precoated with anti-insulin receptor monoclonal antibodies. The plates are then incubated with biotinylated 4G10 (anti-phosphotyrosine antibody, Upstate Biotechnology, Inc, Lake Placid, NY). After incubation for 2 hours at room temperature, the plate is washed free of excess 4G10 and incubated with 100 μl horseradish peroxidase conjugated streptavidin (Zymed laboratories, S. San Francisco, Calif.). The plates are incubated for 30 minutes and excess streptavidin washed away. Substrate (tetraethyl benzidine) is then added and the reaction developed for color. Absorbance is read at 450 nm.

Since the MCF-7 cells are transfected with a cDNA clone containing the full length PC-1 these cells are expected to overexpress the membrane glycoprotein. Normal insulin receptor autophosphorylation is decreased in these cells.

Hybridoma supernatants which restore insulin receptor tyrosine kinase autophosphorylation are selected for further characterization.

For measuring the potential preventative, suppressive or therapeutic benefit of the antibody agents of the present invention certain in vitro and, in vivo clinical outcomes can be assessed. Several additional cellular assays exist that are useful in the context of the present invention. These include the glucose uptake assay utilizing the mouse 3T3-L1 adipocytes Cheatham et al., *Mol. Cell, Bio.*, 14(7):4902–4911 (1994). According to this procedure, potential antibody agents are selected according to their ability to effect insulin-stimulated glucose uptake. The antibody agents of the present invention can also be used to evaluate the ability of insulin to stimulate mitogenesis by assays easily recognized by one of ordinary skill in the art.

Next, the potential antibody agents are screened in a number of different in vivo situations. One skilled in the art will recognize that the agents can be evaluated according to their effects on sensitivity to glucose in appropriate murine models. Several animal model systems testing the therapeutic benefit of the antibody agents of the invention exist. These include models of insulin resistance such as the male obese Wistar Diabetic Fatty rat model of NIDDM (Greene, S., *Obesity Re,*, 2:432 (1994)). The insulin resistant obese diabetic Zucker rat is an animal model of human type 2 NIDDM, Terrettaz and Jeanrenaud, *Endocrinology*, 112:1346–1351 (1983); Haring, H. and Obermaier-Kusser, B., *Diabetes/Metabolism Reviews*, 5:431 (1989).

Additionally, agents can be screened according to their ability to effect any of several in vivo parameters. The spontaneously obese rhesus monkey is a suitable model system for these studies Bodkin et al., *Amer. J. Physiol.*, 256(5 pt.2):E676–681 (1989). According to this model plasma levels of insulin and glucose can be determined, Hansen & Bodkin, *Diabetologia*, 29:713–719 (1986) in the fasting state and following intravenous injection of glucose.

7. Selecting Appropriate Antibodies

Once antibodies of the desired specificity are generated, they may be used to identify and select other antibodies having the same or cross-reactive epitope specificity. For example, a new antibody is tested by measuring its ability to inhibit the binding of an antibody of known specificity to its epitope. Various competitive binding assays known in the art can be used.

The isotype of the antibody can be selected during hybridoma production or by appropriate recombinant methods well-known in the art to achieve a desired effector function mediated by the Fc portion of the immunoglobulin heavy chain. For example, certain isotypes, such as IgG2a, have superior activity in antibody-dependent cellular cytotoxicity. Likewise, certain isotypes, such as IgG2a, are more readily eliminated from the circulation through Fc receptors on cells of the reticuloendothelial system and are therefore more efficient at removing an undesired antigen or target cell from sites of active disease. Accordingly, depending on the intended use, a particular antibody isotype may be preferable to others, as can be readily ascertained by one of ordinary skill in the art without undue experimentation.

To identify a hybridoma producing an antibody of a particular isotype, or to switch an isotype of an antibody, the hybridoma supernatants may be screened for production of PC-1 specific mAbs using an ELISA which tests for the immunoglobulin isotype. What follows is an example of a method for selecting a desired isotype switch from IgG1 to IgG2a. Hybridoma cells are grown in the logarithmic phase for a 2–3 week period prior and then subjected to negative selection using antibody-coated magnetic beads. Super paramagnetic iron oxide particles coated with a goat anti-mouse antibody preparation including all IgG isotype classes (BIOMAG® beads purchased from Advanced Magnetics, Inc.) may be used. For switching an isotype from IgG1 to IgG2a, it is necessary to block the IgG2a binding sites on the antibody-coated beads by incubating with immunoglobulins (of irrelevant specificity) having the IgG2a isotype. About $10^8$ hybridoma cells expressing a variety of isotypes are incubated with such IgG2a-blocked beads. Cells expressing IgG1, IgG2b and IgG3 isotypes bind and are removed magnetically from the population. Such a negative selection step is preferably repeated several times.

The remaining cell population, depleted of IgG1, IgG2b and IgG3 bearing cells, and conversely enriched for IgG2a-bearing cells, is plated in microplates at a cell density of about 1000 cells/well. Using commercially available anti-isotype reagents in an ELISA assay, the wells are screened for IgG2a production; positive clones are replated at 0.3 cells/well followed by another round of screening and re-plating. Using such an approach, approximately 1–5 of $10^7$ cells which have switched isotype are optimally selected. Cells which have switched from IgM to IgG can be selected using a similar approach with the appropriate antibody-coated beads.

The binding affinity of the monoclonal antibody can, for example, be determined by the Scatchard analysis of Munson and Pollard, *Anal. Biochem.*, 107:220 (1980). Antibodies with an affinity for PC-1 of about in the range of $10^8$ M-1 and greater are useful with in the context of the present invention.

After hybridoma cells are identified that produce antibodies of the desired specificity, affinity, and/or activity, the clones may be subcloned by limiting dilution procedures and grown by standard methods (Goding, supra). Suitable culture media for this purpose include, for example, DMEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxyapatite chromatography, gel electrophoresis, dialysis, or affinity chromatography.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., *Curr. Opinion in Immunol.*, 5:256–262 (1993); and Plückthun, *Immunol. Revs.*, 130:151–188 (1992).

The DNA also may be modified, for example, by substituting the coding sequence for human heavy- and light-chain constant domains in place of the homologous murine sequences, Morrison et al., *Proc. Nat. Acad. Sci.*, 81:6851 (1984), or by covalently joining to the immunoglobulin coding sequence all or part of the coding sequence for a non-immunoglobulin poly-peptide. In that manner, "chimeric" or "hybrid" antibodies are prepared that have the binding specificity of an anti-PC-1 monoclonal antibody herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for a PC-1 and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include 2-iminothiol and methyl-4-mercaptobutyrimidate.

8. Humanized antibodies

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers, Jones et al., *Nature*, 321:522–525 (1986); Riechmann et al., *Nature*, 332:323–327 (1988); and Verhoeyen et al., *Science*, 239:1534–1536 (1988), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody, Sims et al., *J. Immunol.*, 151:2296 (1993); and Chothia et al., *J. Mol. Biol.*, 196:901 (1987). Another method uses a particular framework derived from the consensus sequence of all human antibodies of a particular subgroup of light or heavy chains. The same framework may be used for several different humanized antibodies, Carter et al., *Proc, Natl. Acad. Sci. USA*, 89:4285 (1992); and Presta et al., *J. Immuno.*, 151:2623 (1993).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

9. Human antibodies

Human monoclonal antibodies can be made by the hybridoma method. Human myeloma and mouse-human heteromyeloma cell lines for the production of human monoclonal antibodies have been described, for example, by Kozbor, *J. Immunol.*, 133:3001 (1984); Brodeur, et al., *Monoclonal Antibody Prod. Techniques and Applns.*, pp.51–63, Marcel Dekker, Inc., N.Y., (1987); and Boerner et al., *J. Immunol.*, 147:86–95 (1991).

It is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255–258 (1993); and Bruggermann et al., *Year in Immuno.*, 7:33 (1993).

Alternatively, phage display technology, McCafferty et al., *Nature*, 348:552–553 (1990) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson, Kevin S. and Chiswell, David J., *Current Opinion in Structural Biology*, 3:564–571 (1993). Several sources of V-gene segments can be used for phage display. Clackson et al., *Nature*, 352:624–628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.*, 222:581–597 (1991), or Griffith et al., *EMBO J.*, 12:725–734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al. *Bio/Technol.*, 10:779–783 (1992). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the nM range. A strategy for making very large phage antibody repertoires has been described by Waterhouse et al., *Nucl. Acids Res.*, 21:2265–2266 (1993).

Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable capable of restoring a functional antigen-binding site, i.e. the epitope governs (imprints) the choice of partner. When the process is repeated in order to replace the remaining rodent V domain, a human antibody is obtained (see PCT WO 93/06213, published Apr. 1, 1993). Unlike traditional humanization of rodent antibodies by CDR grafting, this technique provides completely human antibodies, which have no framework or CDR residues of rodent origin.

10. Uses for Antibody Agents

Anti-PC-1 antibodies, especially neutralizing antibodies, are useful in diagnostic assays for the presence of PC-1 overexpression, e.g., its production in specific cells, tissues, or serum. For example, PC-1 antibodies can be used for a method for detecting or measuring the amount of an insulin receptor tyrosine kinase inhibitor in a sample comprising the steps of (a) contacting a sample with a first anti-PC-1 antibody under conditions which allow immunospecific binding to occur (b) contacting the sample with a second anti-PC-1 antibody under conditions which allow immunospecific binding to occur; and(c) detecting or measuring any immunospecific binding that occurs of a component of the sample with both the first and the second anti-inhibitor antibodies, in which immunospecific binding of a component of the sample with said first and second antibodies indicates the presence or amount of the inhibitor in the sample.

The invention also includes a method for determining the overexpression of an insulin receptor tyrosine kinase inhibitor in a sample comprising the steps of: (a) measuring the total amount of an insulin receptor tyrosine kinase inhibitor according to the method described supra; and comparing the amount determined in step (a) to an amount of insulin receptor tyrosine kinase inhibitor present in a standard sample, an increased level in the amount of step (a) being indicative of an overexpression of the insulin receptor tyrosine kinase inhibitor.

The invention thus provides a method for detecting the presence or the onset of insulin resistance or non-insulin dependent diabetes mellitus, or other disease or disorder involving inappropriate glucose metabolism comprising the steps of; measuring the amount of an insulin receptor tyrosine kinase inhibitor in a sample according to the method described supra and comparing the amount of the insulin receptor tyrosine kinase inhibitor in the sample to the amount of insulin receptor tyrosine kinase inhibitor in a standard sample, an overabundance of insulin receptor tyrosine kinase inhibitor in the sample being indicative of the disorder.

11. Assays Formats and Kits

Many different assays and assay formats can be used to detect the amount of PC-1 in a sample relative to a control sample. These formats, in turn are useful in the diagnostic assays of the present invention. The diagnostic assays are useful in the identification of diseases and disorders involving increased or abnormal levels of PC-1.

Any procedure known in the art for the measurement of soluble analytes can be used in the practice of the instant invention. Such procedures include but are not limited to competitive and non-competitive assay systems using techniques such as radioimmunoassay, enzyme immunoassays (EIA), preferably the enzyme linked immunosorbent assay (ELISA), "sandwich" immunoassays, precipitin reactions, gel diffusion reactions, immunodiffusion assays, agglutination assays, complement-fixation assays, immunoradiometric assays, fluorescent immunoassays, protein A immunoassays, and immunoelectrophoresis assays, to name but a few. For examples of preferred immunoassay methods, see U.S. Pat. No. 4,845,026 (Jul. 4, 1989) and U.S. Pat. No. 5,006,459 (Apr. 9, 1991).

In one embodiment, one or more of the antibodies used in an assay to bind a PC-1 molecule according to the invention are labeled; in another embodiment, a first is unlabeled, and a labeled, second antibody is used to detect the PC-1 bound to the first antibody. A further method includes the assay where for instance a rat IgG monoclonal antibody is used to detect or measure PC-1(antigen) in a sample by binding thereto Labeled goat anti-rat immunoglobulin can then be used to detect the bound monoclonal antibody.

In a preferred embodiment, polyclonal and/or monoclonal antibodies can be used in sandwich immunoassays according to the invention. In a particular embodiment, a first antibody is not used and the PC-1 is bound directly to a solid support and a second binding partner which is an antibody or antibody fragment or derivative is used in the detection.

In an EIA, the enzymes which can be used to detectably label an antibody include, but are not limited to, horseradish peroxidase, alkaline phosphatase, glucose-6-phosphate dehydrogenase, malate dehydrogenase, staphylococcal nuclease, $\Delta$-V-steroid isomerase, yeast alcohol dehydrogenase, alpha-glycerophosphate dehydrogenase, triose phosphate isomerase, asparaginase, glucose oxidase, X-galactosidase, ribonuclease, urease, catalase, glucoamylase and acetylcholinesterase.

It is also possible to label the detection antibody with a fluorescent compound. When the fluorescently labeled antibody is exposed to light of the proper wavelength, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The detecting antibody can also be detectably labeled using fluorescence emitting metals such as $^{152}$Eu, or others of the lanthanide series. These metals can be attached to the antibody using such metal chelating groups as diethylenetriaminepentaacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester. Likewise, a bioluminescent compound may be used to label the antibody. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Any other label known in the art may be used, e.g., a radionuclide, etc.

In the assays of the present invention, an antigen such as PC-1, or an antibody is preferably bound to a solid phase support or carrier. By "solid phase support or carrier" is intended any support capable of binding an antigen or antibodies. Well-known supports, or carriers, include glass, polystyrene, polypropylene, polyethylene, dextran, nylon, amyloses, natural and modified celluloses, polyacrylamide, agaroses, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

In a preferred embodiment, an antibody-antigen-antibody sandwich immunoassay is done, i.e., antigen is detected or measured by a method comprising binding of a first antibody to the antigen, and binding of a second antibody to the antigen, and detecting or measuring antigen immunospecifically bound by both the first and second antibody. In a specific embodiment, the first and second antibodies are monoclonal antibodies. In this embodiment, if the antigen does not contain repetitive epitopes recognized by the monoclonal antibody, the second monoclonal antibody must bind to a site different from that of the first antibody (as reflected e.g., by the lack of competitive inhibition between the two antibodies for binding to the antigen). In another specific embodiment, the first or second antibody is a polyclonal antibody. In yet another specific embodiment, both the first and second antibodies are polyclonal antibodies.

In a preferred embodiment, a "forward" sandwich enzyme immunoassay is used, as described schematically below. An antibody (capture antibody, Ab1) directed against the PC-1 is attached to a solid phase matrix, preferably a microplate. The sample is brought in contact with the Ab1-coated matrix such that any PC-1 in the sample to which Ab1 is specific binds to the solid-phase Ab1. Unbound sample components are removed by washing. An enzyme-conjugated second antibody (detection antibody, Ab2) directed against a second epitope of the antigen binds to the antigen captured by Ab1 and completes the sandwich. After removal of unbound Ab2 by washing, a chromogenic substrate for the enzyme is added, and a colored product is formed in proportion to the amount of enzyme present in the sandwich, which reflects the amount of antigen in the sample. The reaction is terminated by addition of stop solution. The color is measured as absorbance at an appropriate wavelength using a spectrophotometer. A standard curve is prepared from known concentrations of the antigen, from which unknown sample values can be determined.

Other types of "sandwich" assays are the so-called "simultaneous" and "reverse" assays. A simultaneous assay involves a single incubation step as the antibody bound to the solid support and labeled antibody are both added to the sample being tested at the same time. After the incubation is completed, the solid support is washed to remove the residue of fluid sample and uncomplexed labeled antibody. The presence of labeled antibody associated with the solid support is then determined as it would be in a conventional "forward" sandwich assay.

In the "reverse" assay, stepwise addition first of a solution of labeled antibody to the fluid sample followed by the addition of unlabeled antibody bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays.

Kits comprising one or more containers or vials containing components for carrying out the assays of the present invention are also within the scope of the invention. For instance, such a kit can comprise an antibody or antibodies, preferably a pair of antibodies to the PC-1 antigen which preferably do not compete for the same binding site on the antigen. In a specific embodiment, PC-1 may be pre-adsorbed to the solid phase matrix. The kit preferably contains the other necessary washing reagents well-known in the art. For EIA, the kit contains the chromogenic substrate as well as a reagent for stopping the enzymatic reaction when color development has occurred. The substrate included in the kit is one appropriate for the enzyme conjugated to one of the antibody preparations. These are well-known in the art, and some are exemplified below. The kit can optionally also comprise a PC-1 standard; i.e., an amount of purified PC-1 corresponding to a normal amount of PC-1 in a standard sample.

In a specific embodiment, a kit of the invention comprises in one or more containers: (1) a solid phase carrier, such as a microtiter plate coated with a first antibody; (2) a detectably labeled second antibody; (3) a standard sample of the PC-1 molecule recognized by the first and second binding partners.

12. Additional Antibody Agent Uses

The agent herein may also be used as an affinity purification agent. In this process, the antibodies against the inhibitor are immobilized on a suitable column such as a Sephadex column by any conventional technique. The sample containing the inhibitor to be separated is placed on the column and the column is washed with a suitable solvent that will let all molecules pass except the inhibitor, which adheres to the column. Then the column is washed with a suitable solvent, such as glycine buffer, pH 5.0, to elute the Inhibitor from the column.

The antibodies herein are also useful in a receptor binding or radioreceptor assay in a conventional manner, as by incubating a mixture of radiolabeled inhibitor (e.g., radioiodinated inhibitor) and the antibody with cells containing the insulin receptor, and determining if the antibody blocks binding of the labeled inhibitor to the receptor.

13. Soluble Receptors or Fragments Thereof

In another preferred aspect "agent" is meant to include a portion of an insulin receptor that binds the PC-1 molecule or interferes with the PC-1 interaction with the membrane associated insulin receptor and, by virtue of binding or interfering, neutralizes the effect of the PC-1 on the tyrosine kinase activity of the membrane associated receptor. The soluble receptor may be a portion of the membrane associated insulin receptor such as a peptide or fragment thereof.

According to this aspect of the invention care must be taken to select a soluble insulin receptor that does not bind insulin in vivo but has the desirable quality of preventing the interaction of the PC-1 molecule with the membrane associated insulin receptor. Ideally, the soluble receptor fragment will prevent or block the PC-1 dependant inhibition of the membrane bound insulin receptor tyrosine kinase activity.

Such soluble receptor molecules are based in whole or in part on the insulin receptor primary structure. The primary structure of the insulin receptor as well as the nucleic acid encoding the receptor can be found in U.S. Pat. No. 4,761,371 issued Aug. 2, 1988, by Bell et al.

Soluble insulin receptor constructs can therefore be devised which lack all or a portion of the transmembrane region of the insulin receptor. To this end an expression vector can be constructed to encode an insulin receptor molecule which lacks the carboxyl-terminal transmembrane region. In one embodiment the fragment retains the desirable property of binding PC-1 in vivo. By binding PC-1, the soluble receptor fragment prevents the interaction of the PC-1 with the membrane associated insulin receptor.

Portions of the insulin receptor molecule which are important for the recognition of insulin can be determined by those skilled in the art. Additionally, site-directed mutagenesis such as those techniques described by Kunkel et al., *Methods of Enzymol.* 154:367–382 (1987), as well as alanine scanning mutagenesis as described in Cunningham and Wells, (1989) *Science,* 244:1081–1085 can be employed, as well as other routine techniques, to elucidate the portions of the insulin receptor critical to insulin binding. A soluble molecule based on the primary structure of the insulin receptor that does not bind insulin but which has the desirable quality of preventing the interaction of the PC-1 with the membrane bound insulin receptor can thus be devised.

To this end an expression vector can be constructed to encode a soluble molecule based on the primary sequence of insulin receptor. After the sequence encoding the portion of the insulin receptor having the desirable properties is prepared, expression can be obtained using techniques available to those of skill in the art.

Potential candidates for the soluble molecule can be screened according to their ability to inhibit PC-1 dependent inhibition of insulin receptor tyrosine kinase activity. Assays which monitor the autophosphorylation of the insulin receptor, as well as phosphorylation of exogenous substrates, such as those described herein can be used to select the appropriate soluble receptor molecule.

14. Therapeutic Use of Agents

The preclinical and clinical therapeutic use of the present invention in the treatment of diseases or disorders associated with overexpression of PC-1 will be best accomplished by those of skill, employing accepted principles of diagnosis and treatment. Such principles are known in the art, and are set forth, for example, in Braunwald et al., eds., *Harrison's Prncpls. of Intnl. Med.,* 11th Ed., McGraw-Hill, N.Y. (1987).

The agents of the present invention provide distinct advantages in the treatment of a disease or disorder involving inappropriate PC-1 expression. Prior to the instant invention, therapeutic options for treatment of improper glucose metabolism as a result of insulin resistance included: (a) no treatment with possible spontaneous resolution; (b) treatment with rigorous dietary modification to control postprandial glucose levels c) costly insulin supplementation therapy. The therapeutic methods of the instant invention have the distinct advantage over the prior art methods of treating a disorder associated with improper glucose metabolism as a result of overexpression of membrane glycoprotein PC-1. The methods provide for specific, inexpensive intervention at the probable pathogenic origin of the imbalance.

For therapeutic applications, the agents may be administered to a mammal, preferably a patient, in a pharmaceutically acceptable dosage form, including those that may be administered to a patient intravenously as a bolus or by continuous infusion over a period of minutes, hours, days, weeks, or months, intramuscularly, subcutaneously, intraarticularly, intrasynovially, intrathecally, or periostally, or by oral, topical, or inhalation routes.

The most effective mode of administration and dosage regimen of agent will depend on the type of disease to be treated, the severity and course of the disease, whether the agents are administered for prophylactic or therapeutic purposes, previous therapy, the patient's clinical history and response to the agents such as antibodies, and the discretion of the attending physician. The agent is suitably administered to the patient at one time or over a series of treatments.

A dose of agent may be administered to the patient, whether via, e.g., one or more single administrations, continuous infusion, or bolus injection. For example, an initial dose of the agent is administered to the patient by injection or infusion. For repeated administrations over several days or longer, depending on the condition, the treatment is repeated until a desired suppression of disease symptoms occurs. However, other dosage regimens may be useful. According to another embodiment of the invention, the effectiveness of the agent may be improved by administering the agent serially or in combination with another agent that is effective for this purpose.

Several clinical parameters can be followed over the course of treatment including monitored clinical improvement in 1) glycemic control and consequences thereof including for instance, normalization of serum lipids, and reduced risk for late vascular complication; 2) stabilized glycemic control, for instance, reduced brittleness and reduced risk for acute decompensation; and 3) reduced incidence of diabetic ketoacidosis.

An amount of agent capable of preventing PC-1 dependent inhibition of insulin receptor tyrosine kinase activity when provided to a patient is a "therapeutically effective" amount, which is generally about 0.01 to 100 mg/kg body weight/day depending on the factors noted above. The dosage of an antibody agent may be given by an intravenously injectable dose in the range of about 0.01 to 25 mg/kg body weight/day.

Pharmaceutical Compositions of the Invention

The agents of the present invention including antibodies, and soluble receptor fragments are well suited for the preparation of pharmaceutical compositions. The pharmaceutical compositions of the invention may be administered to any animal which may experience the beneficial effects of the compositions of the invention. Foremost among such animals are humans, although the invention is not intended to be so limited.

In addition to the agent itself pharmacologically active, pharmaceutical compositions preferably contain suitable pharmaceutically acceptable carriers comprising excipients and auxiliaries which facilitate processing of the active compounds into preparations which can be used pharmaceutically.

Suitable formulations for parenteral administration include aqueous solutions of the peptides in water-soluble form, for example, water-soluble salts. In addition, suspensions of the proteins or peptides as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxy-methyl cellulose, sorbitol, and/or dextran. Optionally, the suspension may also contain stabilizers. The agents of the invention are preferably formulated in purified form substantially free of aggregates and other protein materials.

The compositions are formulated using conventional pharmaceutically acceptable parenteral vehicles for administration by injection. These vehicles are nontoxic and therapeutic, and a number of formulations are set forth in *Remington's Pharmaceutical Sciences*, 16th ed., Mack Publishing Co., (1980). Non-limiting examples of excipients are water, saline, Ringer's solution, dextrose solution and Hank's balanced salt solution. Formulations according to the invention may also contain minor amounts of additives such as substances that maintain isotonicity, physiological PH, and stability. Such dosage forms encompass pharmaceutically acceptable carriers that are inherently nontoxic and nontherapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol.

Adjuvants for topical or gel-based forms of agents include polysaccharides such as sodium carboxymethylcellulose or methylcellulose, polyvinylpyrrolidone, polyacrylates, polyoxyethylene-polyoxypropylene-block polymers, polyethylene glycol, and wood wax alcohols.

For all administrations, conventional depot forms are suitably used. Such forms include, for example, microcapsules, nano-capsules, liposomes, plasters, inhalation forms, nose sprays, and sublingual tablets.

The examples that follow demonstrate the present invention. The methods employed herein are exemplary only. It will be apparent that various departures from and modifications of these techniques may be made in light of the present specification and the ordinary level of skill in the art without departing from the spirit and scope of the invention. All literature and patent citations in the examples are expressly incorporated by reference.

EXAMPLES

1. General Methods 1.1 Autophosphorylation of Exogenous Substrate

Insulin-receptor autophosphorylation and insulin-receptor tyrosine kinase activity employing the artificial substrate poly(Glu-Tyr) were carried out according to standard methods. Sbraccia et al., *J. Biol. Chem.* 265:4902–907 (1990). 1 ng insulin receptor was incubated in 25 μl buffer containing 2 mM MnCl$_2$, 10 mM MgCl$_2$, 50 mM HEPES (pH 7.6), 150 mM NaCl, 0.1% TRITON® X-100, and 1% BSA in the presence or absence of 100 nM insulin for 1 h at 20° C. A 5 μl mixture of 1 mg/ml poly(Glu-Tyr) and 10 μM[$^{32}$P]ATP was added for 1 h at 20° C. $^{32}$P incorporation was then measured by trichloroacetic acid precipitability of filter paper.

Example 2

Insulin Receptor Antagonists in Fibroblasts from an NIDDM Patient

Methods

Insulin Receptor Autophosphorylation

Fibroblasts from patients as well as sex and age matched controls were obtained by forearm skin biopsy and grown under standard conditions in Dulbecco's Modified Eagles Medium (DMEM) supplemented with 10% fetal bovine serum at 37° C. in a humidified atmosphere (Tissue Culture: *Methods and Applns.*, Kruse P. F. Jr. et al., Eds., N.Y., Academic (1973). At the point of assay 1 nM insulin was added to cultures containing 1×10$^6$ fibroblast cells for 2 min. The cells were then thrice washed with PBS at 4° C., and scraped into 1 ml of buffer containing 50 mM HEPES (pH 7.6), 150 mM NaCl, 1 mM p-methyl sulfonyl fluoride (PMSF) and 2 mM sodium orthovanadate. Cells were pelleted, and solubilized in the same buffer without NaCl but containing 1% TRITON® X-100. The lysates were immunoabsorbed with a-IR3 (a monoclonal antibody specific to the IGF-I receptor). The depleted lysates were then immunoprecipitated with an anti-insulin receptor antiserum as described in Forsayeth et al., *Diabetes*, 35:837–846 (1986) and immunoprecipitates subjected to SDS-PAGE in an 8–16% gradient gel (NOVEX) under reducing conditions. Proteins were transferred to nitrocellulose and immunoblotted with an antibody to phosphotyrosine (Upstate Biotechnology, Inc.)

Results

To confirm the presence of an inhibitor to insulin receptor tyrosine kinase activity in intact fibroblasts, in vivo tyrosine kinase activity was assessed by insulin receptor β subunit autophosphorylation as described supra. In control fibroblasts, 1 nM insulin stimulated insulin receptor β-subunit autophosphorylation (FIG. 2). Maximal effects were seen at 10 to 100 nM Insulin (FIG. 2). The fibroblasts from the patient with insulin resistance required significantly more insulin to stimulate autophosphorylation of the insulin receptor in vivo.

Example 3

Purification of the Insulin Receptor Tyrosine Kinase Inhibitor PC-1

Fibroblasts (5×10$^8$) from an individual showing marked inhibition of insulin receptor autophosphorylation in vivo were scraped and washed. Cell pellets were solubilized in 50 mM HEPES (pH 7.6), 1 mM PMSF, 2 mM sodium orthovanadate, and 1% TRITONμ X-100. Solubilized lysates were applied to an anti-insulin receptor antibody affinity column, Sbraccia, et al., (1991); *Diabetes*, 40:295–299; and Maddux, B. A., *J. Clin. End. Metab.* 77:73–79 (1993). The passthrough (depleted of insulin receptors) was then applied to a wheat germ agglutinin agarose column (EY Labs). After washing, the bound glycoproteins were eluted with 0.3 M N-acetyl-D-glucosamine in 50 mM HEPES (pH 7.6), 150 mM NaCl, 0.01% Tween-20 and 1 mM PMSF. The glycoproteins were desalted using a Centricon 100 filter (Amicon Corp) and applied to a 1 ml ATP agarose column (Sigma). After washing, proteins were eluted with a NaCl step gradient. Both the wheat germ agglutinin eluate and the 1 M NaCl eluate were subjected to SDS-PAGE followed by silver staining.

Cell Free Insulin Receptor Tryosine Kinase Assay

The purification of PC-1 was followed by the cell free insulin receptor tyrosine kinase assay described below.

1 ng insulin receptor was incubated in 25 μL buffer containing 2 mm $MnCl_2$, 10 mM $MgCl_2$, 50 mM HEPES (pH 7.6), 150 mM NaCl, 0.1% TRITON® X-100, and 0.1% BSA in the presence or absence of 100 nM insulin for 1 h at 20° C. A 5 μL mixture of 1 mg/mL poly(Glu-Tyr) and 10 μM [$^{32}$P]ATP was added for 1 h at 20° C. $^{32}$p incorporation was then measured by trichloroacetic acid precipitability on filter paper. In the initial studies, 5 μL wheat germ purified extracts containing 0.3 ng insulin receptor immunoreactivity were added to ing purified human insulin receptor from transfected 3T3/HIR mouse fibroblasts expressing $10^6$ human insulin receptor/cell Whittaker et al., *Proc. Natl. Acad. Sci. USA*, 84:5237–5241 (1987). For subsequent studies with extracts depleted of receptor, 5 μL of extract containing 200 ng inhibitor protein were added to purified receptors.

Results

The inhibitor was purified using a cell free insulin receptor tyrosine kinase assay to follow the purification process. Solubilized cell lysates were depleted of insulin receptors, and the inhibitor purified to apparent homogeneity by wheat germ affinity chromatography followed by ATP-agarose chromatography.

Figure 3:
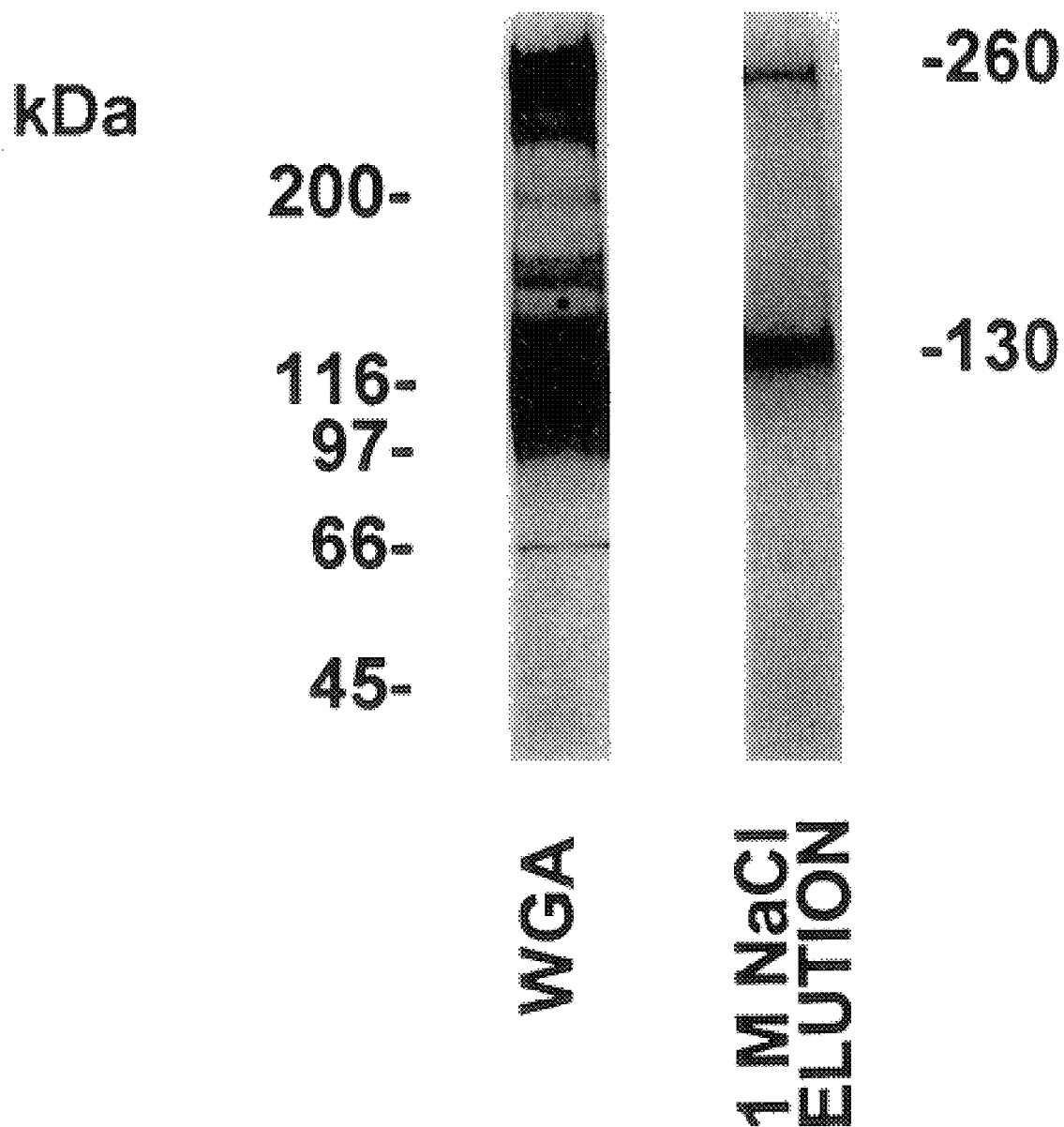
FIG. 3.

The inhibitor eluted from the ATP-agarose column as two bands with relative molecular weights of 130 and 260 kDa (FIG. 3). The ATP-agarose eluate was >100 fold more potent as an inhibitor of insulin receptor tyrosine kinase activity than the wheat germ eluate. Purification from the cell homogenate was >1000 fold as determined by western blotting and enzyme activity.

The 130,000 kDa band was eluted and cleaved with cyanogen bromide; the resulting fragments were separated on a thin SDS gradient gel (0.5 mm) to increase electroblotting transfer efficiency. Bands at 14 and 21 kDa were sequenced (data not shown), and found by Automated Edman degradation to be identical to the corresponding cyanogen bromide peptides of the membrane glycoprotein, PC-1, Buckley et al., *J. Biol. Chem.*, 265:17506–17511 (1990); and Funakoshi, et al., *Arch. Biochem. Biophys.* 295:180–187 (1992).

Example 4

Western Blot Analysis of PC-1 Protein Content in Fibroblasts

Western blotting of lysates from a patent with insulin resistance and NIDDM (MW) cells revealed that there was a 5–10 fold increase in both the 130 kDA (monomer) and 260 kDa (dimer) forms of PC-1 when compared to control cells.

Methods

One μg/lane of inhibitor was electrophoresed in 12% SDS-PAGE using non-reducing sample buffer along with the appropriate controls and standards. The glycoprotein bands were then transferred to a nitrocellulose solid support membrane via semi-dry electrophoretic transfer. The membranes containing transferred glycoproteins were blocked with 1% non-fat dry milk proteins for 2 h or other blocking reagents such as BSA at about 2% and gelatin at about 0.3%. The nitrocellulose membranes were then reacted with polyclonal antibodies to PC-1. The membranes were then washed with buffer (PBS-Tween) 4 times for about 5–10 minutes each. The membranes were then reacted with Horseradish peroxidase labelled anti-murine antibodies for 2 h. The membranes were again washed and subsequently developed with substrate to visualize the glycoprotein bands.

Results

Western blotting of lysates from cells of a patient with insulin resistance and non-insulin dependent diabetes mellitus revealed that there was a 5–10 fold increase in both the 130 kDA (monomer) and 260 kDa (dimer) forms of PC-1 when compared to control cells. The results are demonstrated in FIG. 4A.

Example 5

Northern Blot Analysis of PC-1 mRNA expression

Methods

Fibroblast cells were grown to confluency and 10 μg polyA$^+$ mRNA was prepared by proteinase K digestion (Hartmann et al., *Endocrinology*, 127:2038–2049 (1990). 10 μg poly(A)+ was subjected to 1% agarose formaldehyde electrophoresis, transferred to nitrocellulose, and probed with cDNA's to human PC-1, Warrem et al., *An. Intern. Med.*, 113:909–915 (1990), or B-actin (Hartmann, supra)

Results

In mRNA from MW, there was 5–10 fold increase in the major mRNA species for PC-1 (FIG. 4b); B-actin mRNA was unchanged (FIG. 4c).

Example 6

PC-1 Studies in Dermal Fibroblasts from NIDDM Patients and Controls

Methods

Assay for PC-1 activity: Fibroblasts from controls and NIDDM patients were grown to confluency, washed as described, and solubilized in 150 mM NaCl, 1% Triton X-100, 1 mM PMSF, and 20 mM imidazole (pH 7.8) for 1 h at 4° C. Supernatants containing 0.05–3 μg protein were then incubated with 9 nmol [$^{35}$S]3'-phosphoadenosine, 5'-phosphosulfate (NEN) in the presence of 0.1 μmol $MgCl_2$ in 20 μl buffer (0.1 M 2 amino-2-methyl-1-propanol-HCl, pH 9.4) (Sigma) for 30 min at 37° C. 25 μl 0.1 M sodium acetate (pH 5.5) was added and samples were boiled 1 min. Then 0.5 ml activated charcoal (40 mg charcoal/ml in 20 mM sodium sulfate) was added. After 10 min on ice, tubes were centrifuged, and supernatants counted.

Western Blot analysis: Fibroblasts from 3 controls ($C_1$, $C_2$,$C_3$) and 4 NIDDM patients ($D_1$,$D_2$,$D_3$,$D_4$) were analyzed for PC-1 content by western blot analysis as described above.

Cells were analyzed for insulin receptor B-subunit autophosphorylation as described above.

Results

Figure 5A:
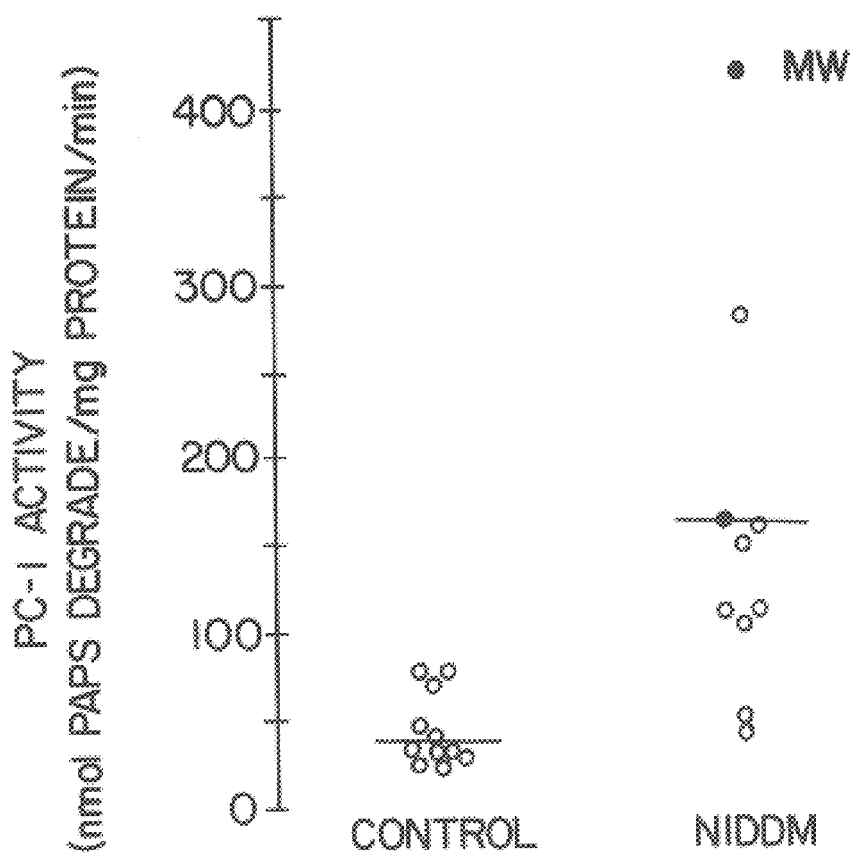
FIGS. 5A–5C.

Since PC-1 has enzyme activity that hydrolyses phosphosulfate bonds, it can be measured using the synthetic substrate 31'-phosphoadenosine, 5'-phosphosulfate (PAPS), Yoshida et al., *J. Biochem.*, 93:1641–1648 (1983). PAPS hydrolysis in fibroblasts from MW was 417 nmoles/mg protein/min, a value 10 fold greater than that of 11 control subjects, 42±7 (mean±SEM, range 22–76) (FIG. 5a). When extracts of Patient fibroblasts and the purified PC-1 protein were treated with an antiserum to PC-1, >900 of both PC-1 activity, and inhibition of insulin receptor tyrosine kinase activity were removed.

Figure 5B:
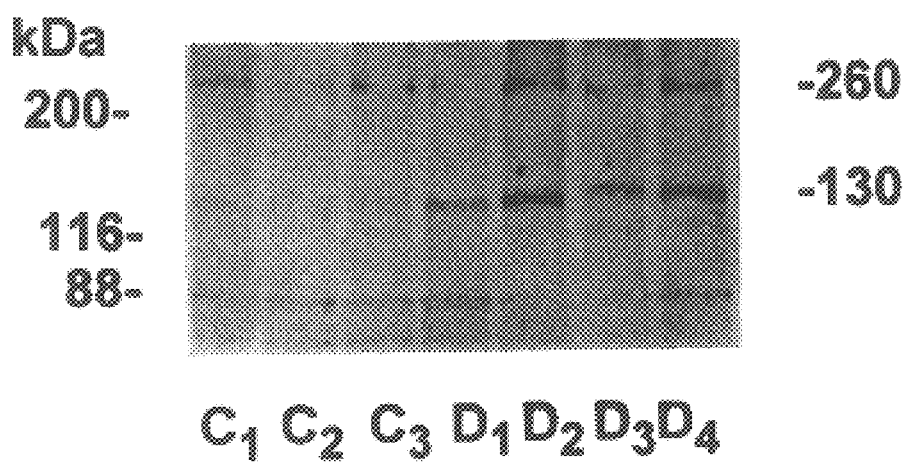
Figure 5C:
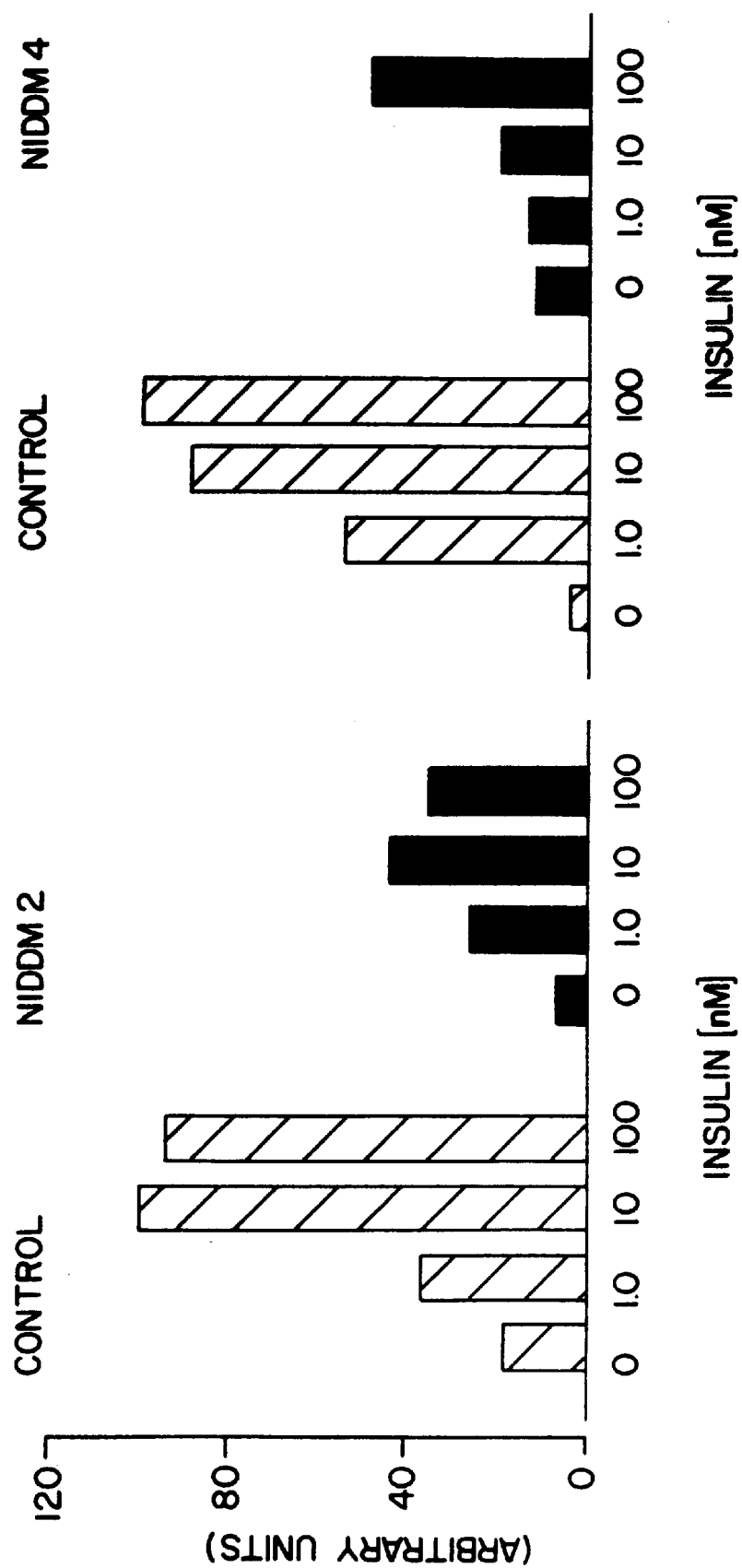

Fibroblasts from 9 additional patients with typical NIDDM (4 males and 5 females) were studied (FIG. 5A). The average age was 51 years (mean), body mass index 28.6±2.7 kg.M$^2$, fasting glucose 223±22 mg/dl; and fasting insulin 29±9 μU/ml. PC-1 activity in the patient fibroblasts was 128±25 nmoles/mg protein/min (mean±SEM); fibroblasts from 2 of the 9 patients gave PC-1 values in the normal range. In 4 patients with high PC-1 activity, we measured fibroblast PC-1 content by Western blotting as described supra. PC-1 was increased when compared to controls (FIG. 5B). PC-1 content was not increased in the 2 NIDDM patients with low PC-1 activity. In fibroblasts from 2 of the patients with high PC-1 activity (D2, D4), insulin receptor tyrosine kinase activity was also decreased (FIG. 5C).

Example 6

Effect of Overexpression on MCF-7 Cells

Methods

Human MCF-7 cells were transfected both with an expression vector, Suva et al., Gene, 77:95–105 (1989), containing the coding sequence of human PC-1, under the control of the cytomegalovirus promoter, and pRK-neo, a selectable marker for neomycin resistance. For controls, MCF-7 cells were transfected with pRK-neo alone. Confluent cells were incubated with 20 pM of $^{125}$I-insulin in the presence or absence of unlabelled insulin, Milazzo et al., Cancer Rsch., 52:3924–3930 (1992), for 18 h at 4° C. Binding to plates was carried out as described in Milazzo et al. supra.

Figure 6A:
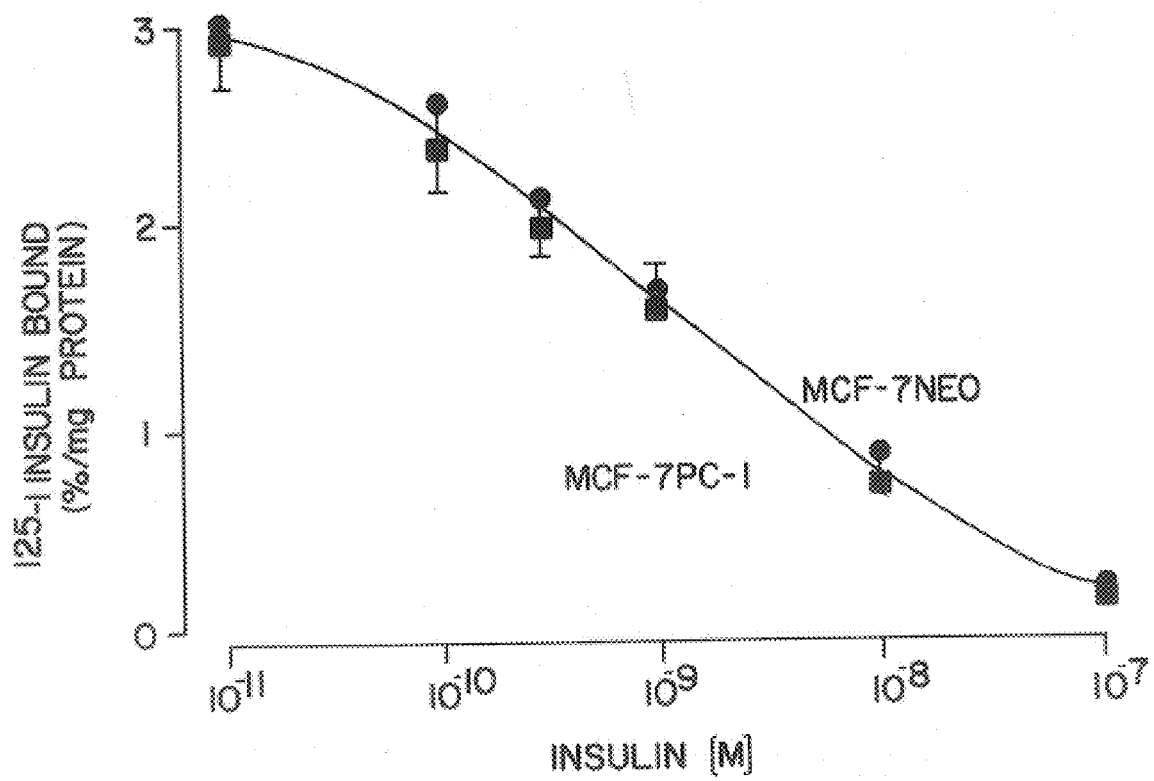
FIGS. 6A–6C.
Figure 6B:
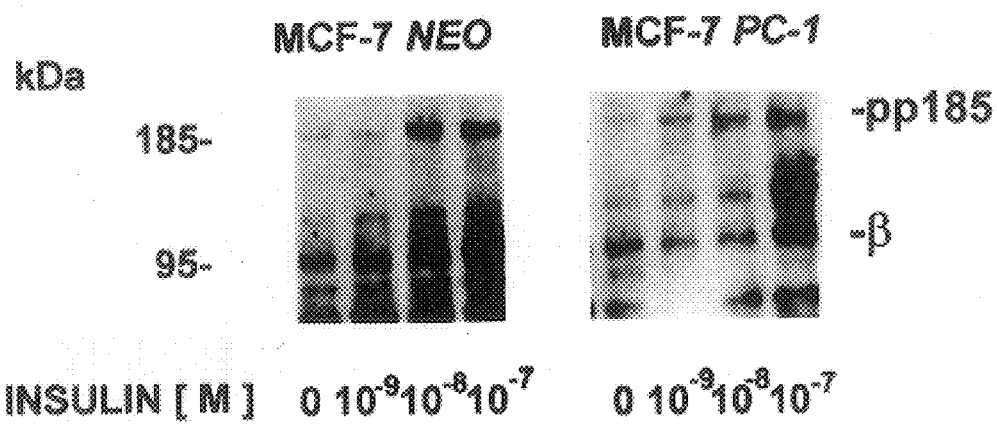

Cells were grown to ~90% confluency, washed, and media was changed to DMEH-21 with 0.1% BSA. Cells were incubated with insulin for 2 min at 37° C., and then solubilized as in Example 2. Lysates were Western blotted as in Example 2, but without prior immunoprecipitation. Shown in FIG. 6B is a representative experiment with pRK-neo transfected and PC-1 transfected MCF-7 cells.

MCF-7 cells were prepared as described above and pre-incubated 16 h with insulin plus 5 nM a-IR3 (an antibody to the IGF-I receptor) to block the IGF-I receptor, and incubated for 2 h with 0.5 mCi/ml of [$^3$H]thymidine. After aspiration and washing, the cells were lysed in 0.03% SDS. The lysates were then treated with 10% trichloroacetic acid, and the [$^3$H]thymidine incorporation measured.

Results

Figure 6C:
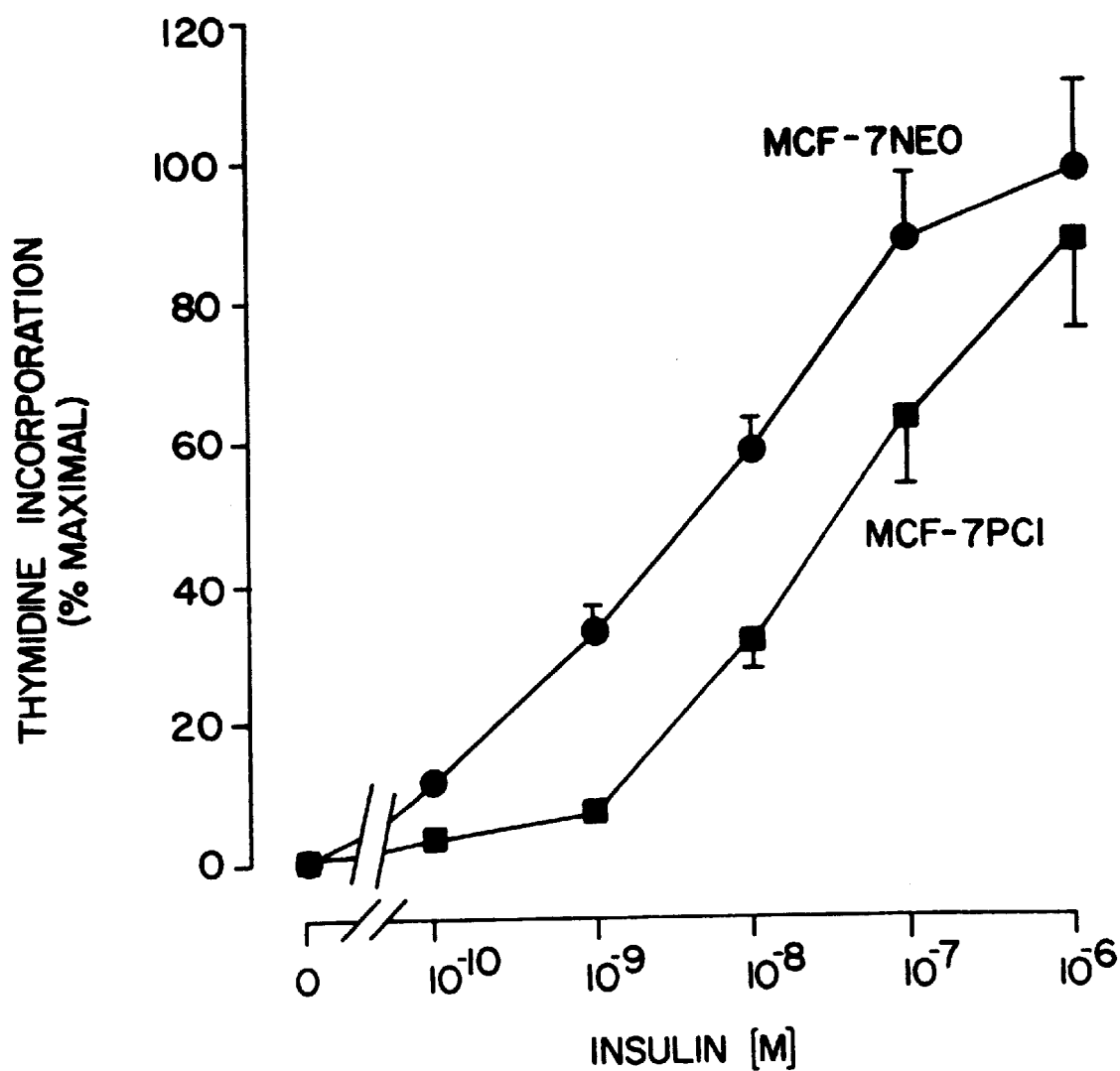

Overexpression of PC-1 in transfected cultured cells reduces insulin stimulated tyrosine kinase activity. MCF-7 cells, a human breast carcinoma cell line that has been utilized for investigating insulin action, were transfected with an expression plasmid containing PC-1 cDNA. Control cells had a PC-1 activity of 10±5 nmoles/mg/min which increased to 405±35 nmoles/mg/min in transfected cells. Overexpression of this protein did not alter insulin receptor binding (FIG. 6A). With PC-1 overexpression, there was marked inhibition of insulin receptor tyrosine kinase activity (FIG. 6B), as measured by both insulin receptor β-subunit autophos-phorylation, and phosphorylation of the intracellular protein, insulin receptor substrate-1 (IRS-I), Myers et al., Diabetes, 42:643–650 (1993). In controls, effects of insulin on both functions were observed at 1 nM, and maximal effects were observed at 10–100 nM. In transfected cells, effects were detected at 10 nM insulin, and at 100 nM the effect of insulin was one half that of controls. In MCF-7 cells, insulin stimulates [$^3$H]thymidine incorporation into DNA, Myers et al., supra) (FIG. 6c). In control MCF-7 cells, this function was half maximally stimulated at approximately 8 fold lower insulin concentrations than in cells overexpressing PC-1.

Example 8

Development of Anti-PC-1 Monoclonal Antibody Agents

A group of three Balb/c female mice (Charles River Breeding Laboratories, Wilmington, Mass.) were injected with 5 µg/dose of purified PC-1 in 100 µl Detox adjuvant (RIBI ImmunoChem Res. Inc., Hamilton, Mont.) by intraperitoneal injection on days 0, 3, 7, 10, and 14. On day 17 the animals were sacrificed, their spleens were removed and the lymphocytes fused with the mouse myeloma line 653, Kearney et al., J. Immunol., 123:1548 (1979) using 50% polyethylene glycol 4000 by an established procedure (Oi and Herzenberg, in Selected Methods in Cellular Immunology, B. Mishel and S. Schiigi, eds., p. 351, W. J. Freeman Co., San Francisco, Calif., (1980). The fused cells were plated into 96-well microtiter plates at a density of 2×10$^5$ cells/well followed by HAT selection, Littlefield, J. W., Science, 145:709 (1964)) on day 1 post fusion.

Immobilized hybridoma culture supernatants were reacted with biotinylated PC-1. The wells positive for anti-PC-1 antibodies were expanded for further study. These cultures remained stable when expanded. Cell lines were cloned by limiting dilution and cryopreserved. The parental cultures were isotyped and assayed for their ability to capture PC-1 and to neutralize in vitro PC-1 activity.

Initially, 13 hybridomas were identified producing antibodies that could bind human PC-1. Of those, one hybridoma designated 4H9.3C7.1C5 was further characterized.

The specificity of the antibody produced by the 4H9.3C7.1C5 hybridoma was tested by direct incubation with PC-1 in a standard ELISA. In this assay wells of a flat bottomed 96 well plate were coated overnight at 4° C. with 100 µl of a solution containing purified human PC-1 at approximately 1 µg/ml in carbonate buffer, pH 9.6. The plate has blocked for 1 h with a solution of 1% BSA in PBS, then washed with wash buffer (0.05% Tween-20 in PBS). Monoclonal antibody purified from ascites generated from hybridoma 4H9.3C7.1C5 as well as isotype matched controls were added to the wells and the plate was incubated for 1–2 hours at room temperature. The wells were washed and a solution containing approximately 1 µg/ml horseradish peroxidase (HRP)-conjugated goat anti-mouse specific antibodies (Cappel, Westchester, Pa.), 0.5% BSA and 0.25% NP-40, in wash buffer was added and the plates incubated for 2 h. After washing, the plates were developed by addition of a solution containing 0.4 µg.ml o-phenylenediamine dihydrochloride plus 0.4/µl/ml 30% hydrogen peroxide. The reaction was stopped by the addition of 2N sulfuric acid. The color reaction was measured at 490 nm with an automated ELISA plate reader.

The results of this assay showed that monoclonal antibody from hybridoma 4H9.3C7.1C5 bound specifically to PC-1, and not appreciably to other proteins.

The isotype of the antibody produced by 4H9.3C7.1C5 was determined by ELISA. Hybridoma cell culture supernatants were added to the wells of microtiter plates that had previously been coated with PC-1. The captured anti-PC1 antibody was incubated with different isotype specific biotin conjugated goat anti-mouse immunoglobulins (Zymed, South San Fransicso, Calif.), and the binding of the conjugated antibodies to the anti PC-1 monoclonal antibody was determined by the addition of streptaviden conjugated with HRP. The color reaction was measured at 405 nm with an ELISA plate reader after addition of substrate.

By this method the isotype of the antibody was determined to be IgG1.

Western blot analysis was conducted according to the following procedure:

a) PC-1 obtained from transfected cells was subjected to SDS-polyacrylamide gel electrophoresis under reducing and non-reducing conditions with the appropriate controls and molecular weight standards.

b) the protein bands were transferred to solid support membranes (nitrocellulose) via semi-dry electrophoretic transfer (Integrated Separation Systems).
c) the membranes containing the transferred proteins were blocked with 1% non-fat dry milk proteins for 2 hr or other blocking material such as bovine serum albumin and gelatin.
d) the membranes were then reacted with anti-PC-1 antibody and isotype matched control antibodies for 2 hr.
e) the membranes were washed with phosphate buffered saline containing 0.05% Tween-20.
f) the membranes were then reacted with HRP-labelled anti-murine antibodies.
g) the membranes were washed.
h) the membranes were incubated with a chemiluminescent substrate (ECL Kit, Amersham) for 1 minute, exposed to x-ray film for 20–120 seconds and the film developed.

In this Western blot analysis, monoclonal antibodies obtained from hybridoma 4H9.3C7.1C5 detected a non-reduced band at approximately 260 kD corresponding to the expected molecular weight of the non-reduced PC-1. The antibody did not detect a band corresponding to the reduced form of the PC-1, suggesting that the monoclonal antibody recognizes a conformational epitope of PC-1.

The antibody was also able to recognize PC-1 expressing cells by flow cytometry. In this procedure MCF 7 cells transfected to express PC-1 on their surface were incubated with anti-PC-1 antibody for 20 min. at 4° C. The cells were washed free of excess anti-PC-1 and incubated with goat anti mouse antibody labelled with fluorescein isothiocyanate (FITC) (TAGO). The cells were incubated for 20 min. on ice and washed free of excess FITC labelled antibody. The cells were fixed in 0.05% paraformaldehyde. Labelled cells were detected using a FACSCAN (Becton Dickenson).

The antibodies are appropriately used in an assay to detect PC-1 expression or PC-1 over expression. The assay can be conducted on any sample suspected of containing human PC-1. Such a sample, for instance, contains dermal fibroblasts of a patient exhibiting insulin resistance. The cells are analyzed by flow cytometry and compared to cells of a normal individual. Alternatively, the cells are lysed with an appropriate lysing reagent and mixed with a known amount of a radio-labelled or otherwise tagged PC-1. In this assay, anti-PC-1 antibodies are mixed with the sample containing the tagged PC-1 and the antibody precipitated using, for instance, a protein A reagent. Tagged PC-1 is measured and a reduction in signal is an indication of the amount of PC-1 present in the sample. This is compared to standard sample for an indication of the amount of PC-1 expressed in the sample.

Example 9

Determination of Affinities of Monoclonal Antibody Agents

The solid-phase radioimmunoassay procedure described by Mariani et al., *J. Immunol. Methods,* 71: 43 (1984) is used to determine the affinities of the inhibitor specific monoclonal antibodies. Briefly, purified anti-inhibitor monoclonal antibodies are coated on Immunlon 2 "Removawell" strips in pH 9.6 carbonate buffer for 18 hours at 4° C. The wells are washed and blocked as described above. 40,000 CPM/well of either $^{125}$I-inhibitor (R & D Systems), in 50 µl PBSG, is added to 2-fold serial dilutions of non-labeled inhibitor ranging from 2500 to 9.7 ng/well, in 50 µl PBSG. The resulting mixture is incubated for 18 hours at 4° C. The wells are washed and counted as described above and the affinity constants determined by Scatchard analysis (Munson and Pollard, supra), which yields similar results as the non-linear regression analysis of Antoni and Mariani, supra.

Example 10

Animal Models

In muscle and fat from male Wistar fatty rats, an animal model of insulin resistance and NIDDM, Greene et al., *Obesity Res.* 2:432–443 (1994), insulin receptor content and insulin receptor tyrosine kinase activity is decreased (Greene et al., supra). In these two tissues, when compared to controls, PC-1 content is elevated by 54 and 74% respectively. Antibodies described herein are injected into these rats and it is expected that their PC-1 activity, as it affects insulin receptor tyrosine kinase activity will be decreased.

Deposit of Materials

The following cultures are being deposited with the American Type Culture Collection, 12301 Parklawn Drive, Rockville, Md., USA (ATCC):

| Hybridoma | ATCC No. | Deposit Date |
| --- | --- | --- |
| 4H9.3C7 | HB11957 | July 19, 1995 |

This deposit is being made under the provisions of the Budapest Treaty on the International Recognition of the Deposit of Microorganisms for the Purpose of Patent Procedure and the Regulations thereunder (Budapest Treaty). This assures maintenance of viable cultures for 30 years from the date of deposit. The organisms will be made available by ATCC under the terms of the Budapest Treaty, and subject to an agreement between Genentech, Inc. and ATCC, which assures permanent and unrestricted availability of the progeny of the cultures to the public upon issuance of the pertinent U.S. patent.

The assignee of the present application agrees that if the cultures on deposit should die or be lost or destroyed when cultivated under suitable conditions, they will be promptly replaced on notification with a viable specimen of the same culture. Availability of the deposited strains are not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the cultures deposited, since the deposited embodiments are intended as an illustration of an aspect of the invention and any cultures that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustration that it represents.

What is claimed is:

1. A method for neutralizing the effect of PC-1 comprising contacting insulin receptor tyrosine kinase inhibitor, class II human membrane glycoprotein PC-1 with an antibody specific for PC-1 in an amount sufficient to effect neutralization.

2. The method according to claim 1 in which the antibody is a monoclonal antibody.

3. The method according to claim 1 in which the method is performed in a mammal.

4. A method for neutralizing the effect of PC-1 comprising contacting insulin receptor tyrosine kinase inhibitor, class II human membrane glycoprotein PC-1 in vitro with an antibody specific for PC-1 in an amount sufficient to effect neutralization.

5. The method according to claim 4 in which the antibody is a monoclonal antibody.

* * * * *

UNITED STATES PATENT AND TRADEMARK OFFICE
CERTIFICATE OF CORRECTION

PATENT NO: 5,968,508
DATED: October 19, 1999
INVENTOR(S): Ira D. Goldfine, et al.

It is certified that error appears in the above-identified patent and that said Letters Patent is hereby corrected as shown below:

Please insert in addition to the Assignee already listed on the face of the patent:

--Genentech, Inc., South San Francisco, California---

Signed and Sealed this

Tenth Day of April, 2001

*Attest:*

NICHOLAS P. GODICI

*Attesting Officer*       *Acting Director of the United States Patent and Trademark Office*

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
       (A) LENGTH: 925 amino acids
       (B) TYPE: amino acid
       (D) TOPOLOGY: linear (xi) SEQUENCE DESCRIPTION: SEQ ID NO:1:

```
Met Glu Arg Asp Gly Cys Ala Gly Gly Ser Arg Gly Gly Glu
  1               5                  10                  15

Gly Gly Arg Ala Pro Arg Glu Gly Pro Ala Gly Asn Gly Arg Asp
                 20                  25                  30

Arg Gly Arg Ser His Ala Ala Glu Ala Pro Gly Asp Pro Gln Ala
                 35                  40                  45

Ala Ala Ser Leu Leu Ala Pro Met Asp Val Gly Glu Glu Pro Leu
                 50                  55                  60

Glu Lys Ala Ala Arg Ala Arg Thr Ala Lys Asp Pro Asn Thr Tyr
                 65                  70                  75

Lys Val Leu Ser Leu Val Leu Ser Val Cys Val Leu Thr Thr Ile
                 80                  85                  90

Leu Gly Cys Ile Phe Gly Leu Lys Pro Ser Cys Ala Lys Glu Val
                 95                 100                 105

Lys Ser Cys Lys Gly Arg Cys Phe Glu Arg Thr Phe Gly Asn Cys
                110                 115                 120

Arg Cys Asp Ala Ala Cys Val Glu Leu Gly Asn Cys Cys Leu Asp
                125                 130                 135

Tyr Gln Glu Thr Cys Ile Glu Pro Glu His Ile Trp Thr Cys Asn
                140                 145                 150

Lys Phe Arg Cys Gly Glu Lys Arg Leu Thr Arg Ser Leu Cys Ala
                155                 160                 165

Cys Ser Asp Asp Cys Lys Asp Lys Gly Asp Cys Cys Ile Asn Tyr
                170                 175                 180

Ser Ser Val Cys Gln Gly Glu Lys Ser Trp Val Glu Glu Pro Cys
                185                 190                 195

Glu Ser Ile Asn Glu Pro Gln Cys Pro Ala Gly Phe Glu Thr Pro
                200                 205                 210

Pro Thr Leu Leu Phe Ser Leu Asp Gly Phe Arg Ala Glu Tyr Leu
                215                 220                 225

His Thr Trp Gly Gly Leu Leu Pro Val Ile Ser Lys Leu Lys Lys
                230                 235                 240

Cys Gly Thr Tyr Thr Lys Asn Met Arg Pro Val Tyr Pro Thr Lys
                245                 250                 255

Thr Phe Pro Asn His Tyr Ser Ile Val Thr Gly Leu Tyr Pro Glu
                260                 265                 270

Ser His Gly Ile Ile Asp Asn Lys Met Tyr Asp Pro Lys Met Asn
                275                 280                 285

Ala Ser Phe Ser Leu Lys Ser Lys Glu Lys Phe Asn Pro Glu Trp
                290                 295                 300

Tyr Lys Gly Glu Pro Ile Trp Val Thr Ala Lys Tyr Gln Gly Leu
                305                 310                 315
```

-continued

```
Lys Ser Gly Thr Phe Phe Trp Pro Gly Ser Asp Val Glu Ile Asn
                320                 325                 330

Gly Ile Phe Pro Asp Ile Tyr Lys Met Tyr Asn Gly Ser Val Pro
                335                 340                 345

Phe Glu Glu Arg Ile Leu Ala Val Leu Gln Trp Leu Gln Leu Pro
                350                 355                 360

Lys Asp Glu Arg Pro His Phe Tyr Thr Leu Tyr Leu Glu Glu Pro
                365                 370                 375

Asp Ser Ser Gly His Ser Tyr Gly Pro Val Ser Ser Glu Val Ile
                380                 385                 390

Lys Ala Leu Gln Arg Val Asp Gly Met Val Gly Met Leu Met Asp
                395                 400                 405

Gly Leu Lys Glu Leu Asn Leu His Arg Cys Leu Asn Leu Ile Leu
                410                 415                 420

Ile Ser Asp His Gly Met Glu Gln Gly Ser Cys Lys Lys Tyr Ile
                425                 430                 435

Tyr Leu Asn Lys Tyr Leu Gly Asp Val Lys Asn Ile Lys Val Ile
                440                 445                 450

Tyr Gly Pro Ala Ala Arg Leu Arg Pro Ser Asp Val Pro Asp Lys
                455                 460                 465

Tyr Tyr Ser Phe Asn Tyr Glu Gly Ile Ala Arg Asn Leu Ser Cys
                470                 475                 480

Arg Glu Pro Asn Gln His Phe Lys Pro Tyr Leu Lys His Phe Leu
                485                 490                 495

Pro Lys Arg Leu His Phe Ala Lys Ser Asp Arg Ile Glu Pro Leu
                500                 505                 510

Thr Phe Tyr Leu Asp Pro Gln Trp Gln Leu Ala Leu Asn Pro Ser
                515                 520                 525

Glu Arg Lys Tyr Cys Gly Ser Gly Phe His Gly Ser Asp Asn Val
                530                 535                 540

Phe Ser Asn Met Gln Ala Leu Phe Val Gly Tyr Gly Pro Gly Phe
                545                 550                 555

Lys His Gly Ile Glu Ala Asp Thr Phe Glu Asn Ile Glu Val Tyr
                560                 565                 570

Asn Leu Met Cys Asp Leu Leu Asn Leu Thr Pro Ala Pro Asn Asn
                575                 580                 585

Gly Thr His Gly Ser Leu Asn His Leu Leu Lys Asn Pro Val Tyr
                590                 595                 600

Thr Pro Lys His Pro Lys Glu Val His Pro Leu Val Gln Cys Pro
                605                 610                 615

Phe Thr Arg Asn Pro Arg Asp Asn Leu Gly Cys Ser Cys Asn Pro
                620                 625                 630

Ser Ile Leu Pro Ile Glu Asp Phe Gln Thr Gln Phe Asn Leu Thr
                635                 640                 645

Val Ala Glu Glu Lys Ile Ile Lys His Glu Thr Leu Pro Tyr Gly
                650                 655                 660

Arg Pro Arg Val Leu Gln Lys Glu Asn Thr Ile Cys Leu Leu Ser
                665                 670                 675

Gln His Gln Phe Met Ser Gly Tyr Ser Gln Asp Ile Leu Met Pro
                680                 685                 690

Leu Trp Thr Ser Tyr Thr Val Asp Arg Asn Asp Ser Phe Ser Thr
                695                 700                 705

Glu Asp Phe Ser Asn Cys Leu Tyr Gln Asp Phe Arg Ile Pro Leu
                710                 715                 720
```

-continued

```
Ser Pro Val His Lys Cys Ser Phe Tyr Lys Asn Asn Thr Lys Val
            725                 730                 735

Ser Tyr Gly Phe Leu Ser Pro Pro Gln Leu Asn Lys Asn Ser Ser
            740                 745                 750

Gly Ile Tyr Ser Glu Ala Leu Leu Thr Thr Asn Ile Val Pro Met
            755                 760                 765

Tyr Gln Ser Phe Gln Val Ile Trp Arg Tyr Phe His Asp Thr Leu
            770                 775                 780

Leu Arg Lys Tyr Ala Glu Glu Arg Asn Gly Val Asn Val Val Ser
            785                 790                 795

Gly Pro Val Phe Asp Phe Asp Tyr Asp Gly Arg Cys Asp Ser Leu
            800                 805                 810

Glu Asn Leu Arg Gln Lys Arg Arg Val Ile Arg Asn Gln Glu Ile
            815                 820                 825

Leu Ile Pro Thr His Phe Phe Ile Val Leu Thr Ser Cys Lys Asp
            830                 835                 840

Thr Ser Gln Thr Pro Leu His Cys Glu Asn Leu Asp Thr Leu Ala
            845                 850                 855

Phe Ile Leu Pro His Arg Thr Asp Asn Ser Glu Ser Cys Val His
            860                 865                 870

Gly Lys His Asp Ser Ser Trp Val Glu Glu Leu Leu Met Leu His
            875                 880                 885

Arg Ala Arg Ile Thr Asp Val Glu His Ile Thr Gly Leu Ser Phe
            890                 895                 900

Tyr Gln Gln Arg Lys Glu Pro Val Ser Asp Ile Leu Lys Leu Lys
            905                 910                 915

Thr His Leu Pro Thr Phe Ser Gln Glu Asp
            920                 925
```